(12) United States Patent
Grinstaff et al.

(10) Patent No.: US 8,367,845 B2
(45) Date of Patent: Feb. 5, 2013

(54) IONIC VISCOELASTICS AND VISCOELASTIC SALTS

(75) Inventors: Mark W. Grinstaff, Brookline, MA (US); Michel Wathier, Brookline, MA (US)

(73) Assignee: The Trustees of Boston University, Boston, MA (US)

( * ) Notice: Subject to any disclaimer, the term of this patent is extended or adjusted under 35 U.S.C. 154(b) by 590 days.

(21) Appl. No.: 12/297,756

(22) PCT Filed: Apr. 20, 2007

(86) PCT No.: PCT/US2007/067047
§ 371 (c)(1),
(2), (4) Date: Oct. 20, 2008

(87) PCT Pub. No.: WO2007/124397
PCT Pub. Date: Nov. 1, 2007

(65) Prior Publication Data
US 2009/0176956 A1    Jul. 9, 2009

Related U.S. Application Data

(60) Provisional application No. 60/793,978, filed on Apr. 21, 2006.

(51) Int. Cl.
*C07D 403/02* (2006.01)
(52) U.S. Cl. .................................. 548/312.7
(58) Field of Classification Search ............... 548/312.7
See application file for complete search history.

(56) References Cited

U.S. PATENT DOCUMENTS

| | | |
|---|---|---|
| 4,501,834 A | 2/1985 | Su |
| 4,735,731 A | 4/1988 | Rose et al. |
| 4,806,256 A | 2/1989 | Rose et al. |
| 4,808,727 A | 2/1989 | Link |
| 5,066,753 A | 11/1991 | Peiffer |
| 5,077,414 A | 12/1991 | Arduengo, III |
| 5,093,448 A | 3/1992 | Peiffer |
| 5,182,405 A | 1/1993 | Arduengo, III |
| 5,258,137 A | 11/1993 | Bonekamp et al. |
| 5,300,279 A | 4/1994 | Simon et al. |
| 5,972,326 A | 10/1999 | Galin et al. |
| 6,350,721 B1 | 2/2002 | Fu et al. |
| 6,531,241 B1 | 3/2003 | McEwen |
| 6,924,253 B2 | 8/2005 | Palmer et al. |
| 2004/0054041 A1 | 3/2004 | Schmidt |

FOREIGN PATENT DOCUMENTS

| | | |
|---|---|---|
| EP | 0 325 818 | 8/1989 |
| WO | WO-2006/012513 | 2/2006 |

OTHER PUBLICATIONS

Database Beilstein [Online] Beilstein Institute for Organic Chemistry, Frankfurt-Main, DE, 1952, XP002601959.
Holbrey et al., "Mercury(II) partitioning from aqueous solutions with a new, hydrophobic ethylene-glycol functionalized bis-imidazolium ionic liquid," Green Chemistry, 5:129-135 (2003).
Hu et al., "Silver Complexes of a Novel Tripodal N-Heterocyclic Carbene Ligand: Evidence for Signifcant Metal-Carbene π-Interaction," Organometallics, 22(4):612-614 (2003).
Jin et al., "Polyethylene glycol functionalized dicationic ionic liquids with alkyl or polyfluoroalkyl substituents as high temperature lubricants," J. Mater. Chem., 16:1529-1535 (2006).
Lynch, D., "Tris(2-ammonioethyl)amine benzene-1,3,5-tricarboxylate 5.5-hydrate," Acta Cryst., E59:1076-1078 (2003) XP-002601957.
Satake et al., "The Micellar Properties of Iionic Surfactants Consisting of the α, ω-Type Surfactant Ion and the Same Type Counter Ion," Bull. Chem. Soc. Jpn., 70(4):761-765 (1997).
Supplementary European Search Report dated Oct. 13, 2010 from EP 07 76 0982.
Han, X.; Armstrong, D. W. "Using Geminal Dicationic Ionic Liquids as Solvents for High-Temperature Organic Reactions," Org. Lett. 2005, 7(19), 4205-4208.
International Search Report in PCT/US2007/067047 mailed Oct. 2, 2008.

*Primary Examiner* — Robert Havlin
(74) *Attorney, Agent, or Firm* — Foley Hoag, LLP

(57) ABSTRACT

One embodiment of the present invention relates to ionic liquids and ionic viscoelastics formed between [1] a small molecule or macromolecule containing two or more cations; and [2] a small molecule or macromolecule containing two or more anions. Another embodiment of the invention is the use of the inventive ionic liquids and ionic viscoelastics, formed between a small molecule or macromolecule containing two or more cations and a small molecule or macromolecule containing two or more anions, to form a crosslinked network. In certain embodiments, the ionic liquids formed can be viscous liquids, viscous liquid formed networks, or viscoelastic networks/gels. In certain embodiments, the ionic material of the invention may be used for a variety of applications including, but not limited to, lubricants, additives, gas separation, liquid separation, membranes, fuel cells, sensors, batteries, coatings, heat storage, liquid crystals, biocompatible fluids, solvents, and electronic materials.

3 Claims, 6 Drawing Sheets

Previous ionic liquids

Additional multi-cationic architectures

[A]

Additional multi-anionic architectures

[B]

IONIC VISCOELASTICS AND VISCOELASTIC SALTS

RELATED APPLICATIONS

This application is the National Stage of International Application No. PCT/US2007/067047, filed Apr. 20, 2007; which claims the benefit of priority to U.S. Provisional Patent Application Ser. No. 60/793,978, filed Apr. 21, 2006.

BACKGROUND OF THE INVENTION

Ionic liquids are "salt-like" materials that are liquid at relatively low temperatures (less than 400° C.). Welton, T. *Chem. Rev.* 1999, 99, 2071-2083; Binnemans, K. *Chem. Rev.* 2005, 105, 4148-4204. Today most scientists consider an ionic liquid a salt that is a liquid below 100° C. Many of the common ionic liquids have melting points at room temperature or below. The first ionic liquids prepared were corrosive materials that had limited utility. In the early 1990s, Wilkes reported a less corrosive air-stable ionic material; this result has provided the impetus for much of the research and development focused on ionic liquids. Wilkes, J. S.; Zaworotko. M. *J. Chem. Commun.* 1992, 965-967.

Ionic liquids are typically composed of a mono-cationic organic compound, such as a compound based on the structure of a imidazolium, pyridinium, pyrrolidinium, phosphonium, ammonium or sulfonium, and an inorganic or organic anion, such as a alkyl sulfate, tosylate, methansulfonate, hexafluorophosphate, tetrafluoroborate, halide, or carboxylic acid. For example, the prototypical ionic liquid of 1-ethyl-3-methylimidazolium ethyl sulfate has a melting point of less than 20° C.; whereas, sodium chloride has a melting point of 801° C. The strong ionic interaction between these mono-cations and mono-anions results in low vapor pressure, non-flammable materials with high thermal, mechanical, and electrochemical stability. More recently, a dicationic organic compound with two mono-anions has been reported. Han, X.; Armstrong, D. W. *Org. Lett.* 2005, 7(19), 4205-4208.

Ionic liquids have found uses in a wide range of applications including, but not limited to, lubricants, MADLI-tof matrices, protein crystallization matrices, solvents for heterogeneous catalysis, solvents for homogeneous catalysis, solvent for organic synthesis, solvents for desulfurization, liquid crystals, thermal fluids, fuel cells, sensors, metal finishers, materials for gas separations, distillation fluids, extraction mediums, and membrane technology.

Viscoelastic materials are semi-solid materials which exhibit solid and liquid like properties depending on temperature, as well as upon being subjected to stress and strain over time. These materials act like elastic solids under some conditions and viscous liquids under others. In other words, viscoelastic materials are materials that show hysteresis in their stress-strain curves. Many plastics and crosslinked polymers are viscoelastic materials. Examples that highlight the diversity of known viscoelastic materials are skin, most of the soft tissue in the body, and the memory foam which is found in matrices.

SUMMARY OF THE INVENTION

One embodiment of the present invention relates to ionic liquids and ionic viscoelastics formed between [1] a small molecule or macromolecule containing two or more cations; and [2] a small molecule or macromolecule containing two or more anions. In certain embodiments, the inventive material is formed between structurally similar cationic and anionic molecules/macromolecules. In other embodiments, the inventive material is formed between structurally dissimilar cationic and anionic molecules/macromolecules. The ionic materials of the invention are liquids or viscoelastics below 400° C. In certain embodiments, the ionic materials of the invention are hydrophobic. In certain embodiments, the ionic materials of the invention are hydrophilic. In certain embodiments, the ionic materials of the invention are halogenated (e.g. fluorinated).

Another embodiment of the invention is the use of the inventive ionic liquids and ionic viscoelastics, formed between a small molecule or macromolecule containing two or more cations and a small molecule or macromolecule containing two or more anions, to form a crosslinked network. In certain embodiments, the ionic liquids formed can be viscous liquids, viscous liquid formed networks, or viscoelastic networks/gels. In certain embodiments, the ionic material of the invention may be used for a variety of applications including, but not limited to, lubricants, additives, gas separation, liquid separation, membranes, fuel cells, sensors, batteries, coatings, heat storage, liquid crystals, biocompatible fluids, solvents, and electronic materials.

DETAILED DESCRIPTION OF THE INVENTION

Figure 1:
FIG. 1 depicts graphically the composition of certain ionic liquids, which were composed of a mono-cation and a mono-anion, or a di-cation and two mono-anions.
Figure 1:
Figure 3:
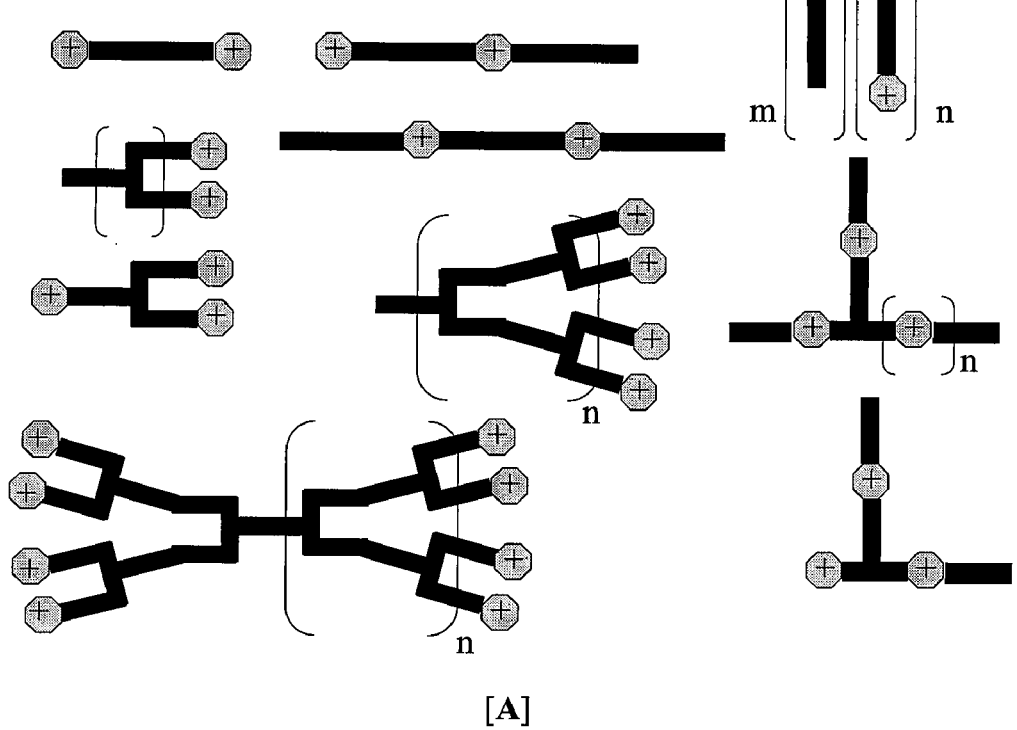
FIG. 3 depicts additional [A] multi-cationic and [B] multi-anionic architectures of the invention.
Figure 3:
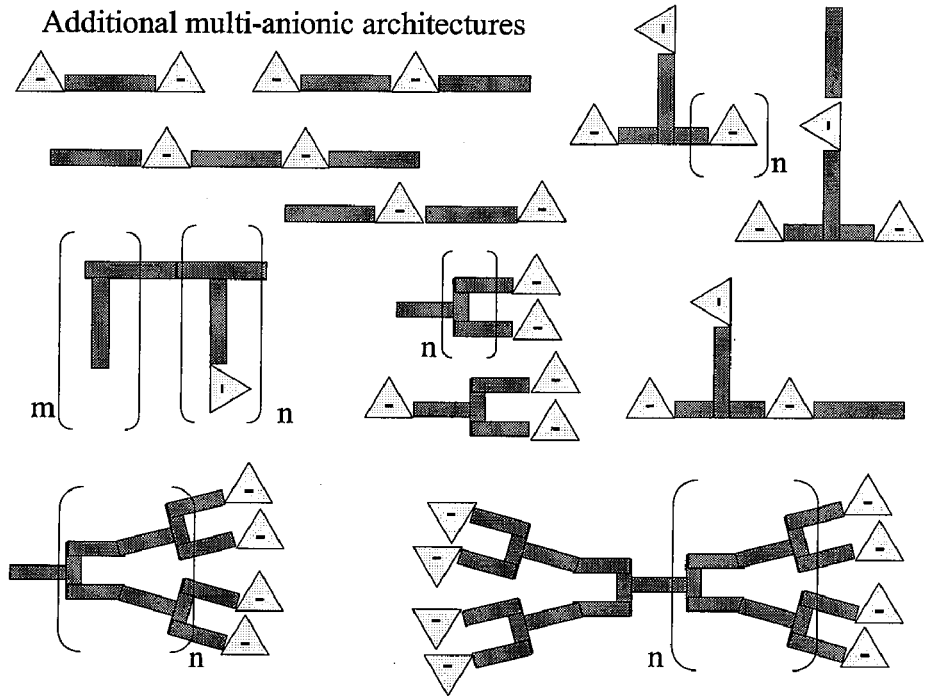
Figure 4:
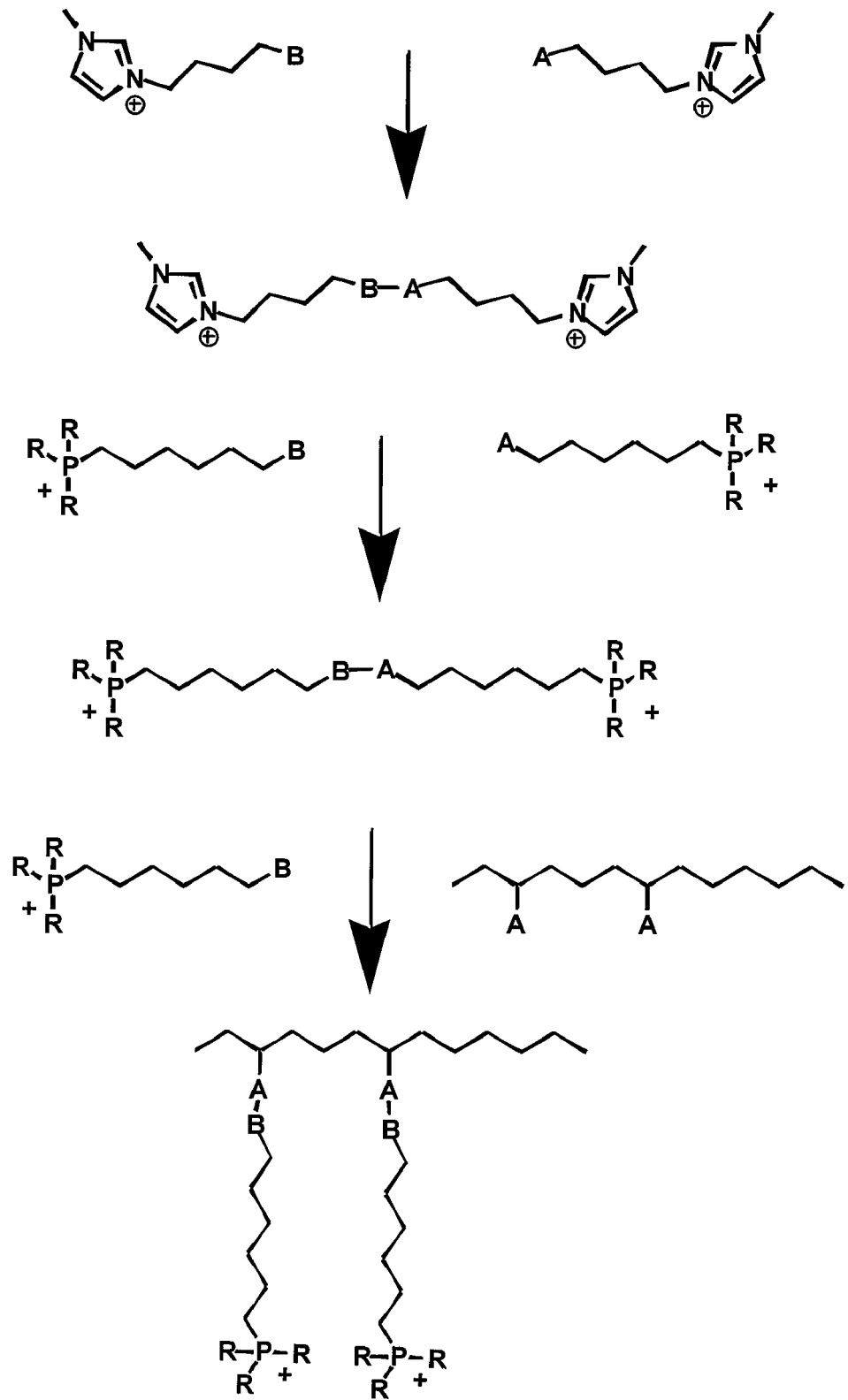
FIG. 4 depicts selected approaches to forming cationic and anionic components of the invention.

One embodiment of the invention relates to the preparation and use of ionic liquids and ionic viscoelastics composed of multi-cationic molecules/macromolecules and multi-anionic molecules/macromolecules. The electrostatic interactions between the cations and anions creates a viscous liquid or viscoelastic material. Selected molecule and macromolecule architectures disclosed in this application are shown in FIGS. 3 and 4. In contrast to previous ionic liquids, ionic materials include the interaction of multi-cationic and multi-anionic centers. As exemplified in FIG. 1, many previous ionic liquids were composed of a single cation and single anion.

Figure 2A:
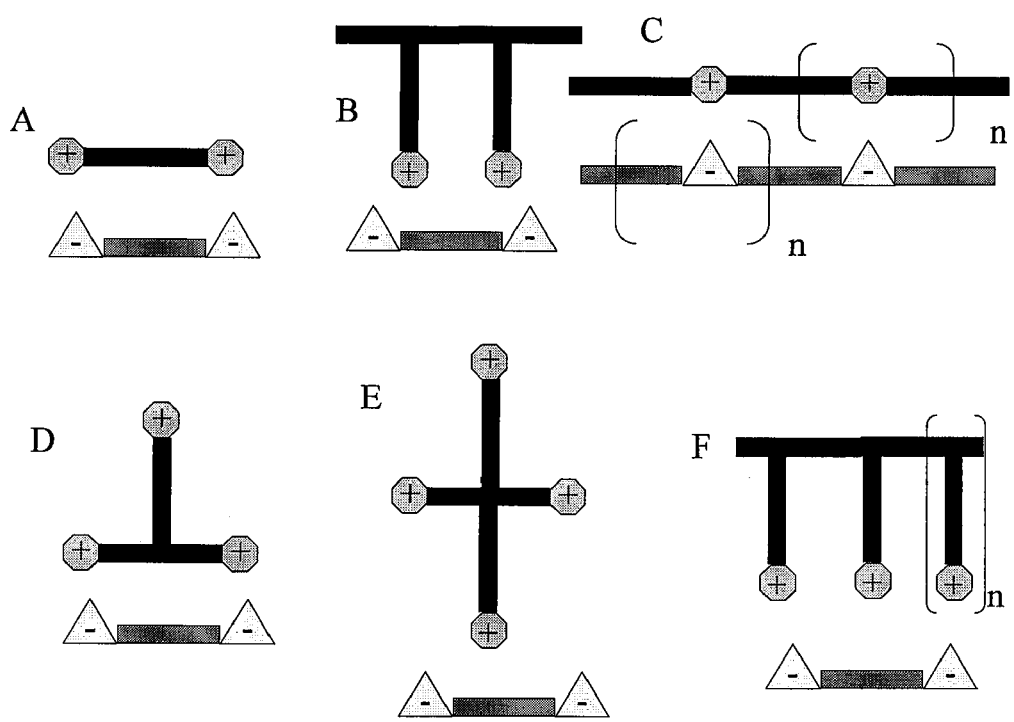
FIGS. 2A, 2B, and 2C depict selected architectures of the multi-cationic and multi-anionic molecules and macromolecules of the invention. The variables n and r are integers.
Figure 2B:
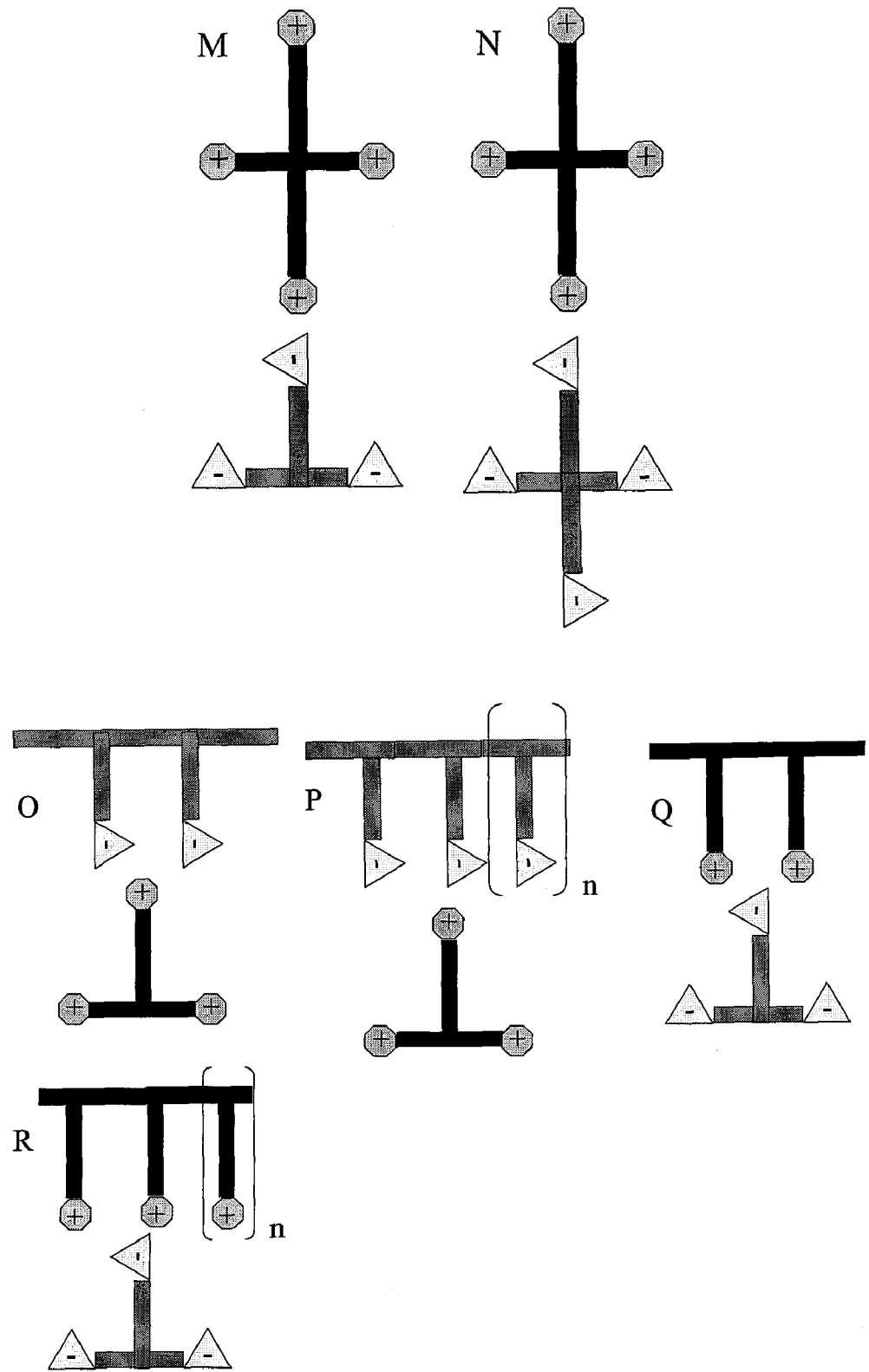
Figure 2C:
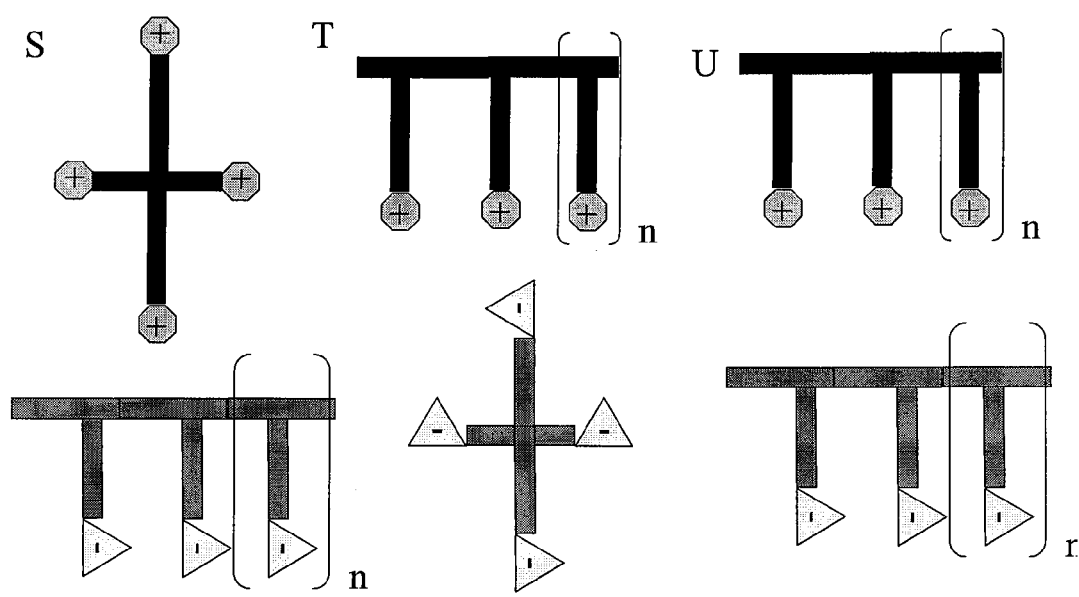

As shown in FIG. 2, there are a wide variety of architectures available for the preparation of the ionic liquids or ionic viscoelastics of the present invention. Structure A represents one of the simplest architecture which is the combination of a dication and dianion to form the ionic liquid. To form an ionic viscoelastic requires a system where at least one of the anionic or cationic molecule or macromolecule is at least a di-cation or di-anion and the other is at least a tri-cation or tri-anion. Architecture D shows such a combination where a tri-cation is combined with a di-anion to create an ionic viscoelastic.

The multi-cations and multi-anions can possess additional structures as shown in FIG. 3. Each of these multi-cationic and multi-anionic molecules/macromolecules can be combined with one or more of each other to prepare an ionic liquid or ionic viscoelastic. The multi-cation and multi-anion molecules and macromolecules of the present invention may comprise one or more than one type of cation and anion, respectively. For example, in a dication both cationic moieties may be the same or they may be different; in a dianion both anionic moieties may be the same or they may be different.

Selected Salts of the Invention. In certain embodiments, the ionic liquids and ionic viscoelastics of the invention include a plurality of organic cations that contain independently for each occurrence a heterocycle selected from the group consisting of azathiozoles, pyrazoles, thiazoles, isothiazoles, oxothiazoles, oxazines, oxazolines, oxazoboroles, dithioazoles, triazoles, selenozoles, oxaphopholes, pyrroles, boroles, furans, thiophenes, pholes, pentazoles, indoles, indolines, oxazoles, isoozazoles, isotriazoles, tetrazoles, benzofurans, dibenzofurans, benzothiophenes, dibenzothiophenes, thiadiazoles, pyrimidines, pyrazines, pyridazines, piperazines, pipidines, morpholenes, pyrans, annolines, phthalzines, quinazolines, quinoxalines, quinolines, isoquinolines, thazines, oxazines, and azaannulenes. Acyclic organic cations are also included in the invention; for example, amines such as amidines, imines, guanidines, phosphines such as phosphinimines, arsines, stibines, ethers, thioethers, and selenoethers.

In certain embodiments, the ionic liquids and ionic viscoelastics described in this invention include a plurality of organic and inorganic anions that contain independently for each occurrence a carboxylic acid, sulfonic acid, tetrafluoroborate, hexafluorophosphate, bis-trifluoromethanesulfonimide, and derivatives thereof. Additional anionic species of the invention include borates, phosphates, nitrates, sulfates, triflates, antimonates, phosphoniums, carboranes, poly-oxo metallates, and metalloboranes.

One aspect of the invention relates to salt comprising an anionic component and a cationic component, wherein:

said anionic component is Y or X—[Y]$_m$;

m is 1-100 inclusive;

X is selected from the group consisting of linear or branched alkanes, linear or branched alkenes, linear or branched alkynes, monocyclic or polycyclic aromatics, monocyclic or polycyclic heteroaromatics, linear or branched polysilanes, linear or branched polyethylene glycols, linear or branched poly(propylene glycol), linear or branched polyalkylene oxides, linear or branched polysiloxanes, linear or branched polyacrylates, linear or branched polyacetals, linear or branched acrylics, linear or branched cellulosics, linear or branched polyethers, linear or branched halogenated polyethers, linear or branched halocarbons, linear or branched polyamides, linear or branched polycarbonates, linear or branched polyethylenes, linear or branched polypropylenes, linear or branched polystyrenes, and linear or branched polyurethanes, or a combination thereof;

Y is selected, independently for each occurrence, from the group consisting of carboxylic acids, sulfonic acids, tetrafluoroborates, hexafluorophosphates, bis-trifluoromethane-sulfonimides, borates, phosphates, nitrates, sulfates, triflates, antimonates, phosphoniums, carboranes, poly-oxo metallates, and metalloboranes;

said cationic component is W—[Z]$_n$;

n is 1-100 inclusive;

W is absent, or selected from the group consisting of linear or branched alkanes, linear or branched alkenes, linear or branched alkynes, monocyclic or polycyclic aromatics, monocyclic or polycyclic heteroaromatics, linear or branched polysilanes, linear or branched polyethylene glycols, linear or branched poly(propylene glycol), linear or branched polyalkylene oxides, linear or branched polysiloxanes, linear or branched polyacrylates, linear or branched polyacetals, linear or branched acrylics, linear or branched cellulosics, linear or branched polyethers, linear or branched halogenated polyethers, linear or branched halocarbons, linear or branched polyamides, linear or branched polycarbonates, linear or branched polyethylenes, linear or branched polypropylenes, linear or branched polystyrenes, and linear or branched polyurethanes, or a combination thereof;

Z is selected, independently for each occurrence, from the group consisting of hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, cyano,

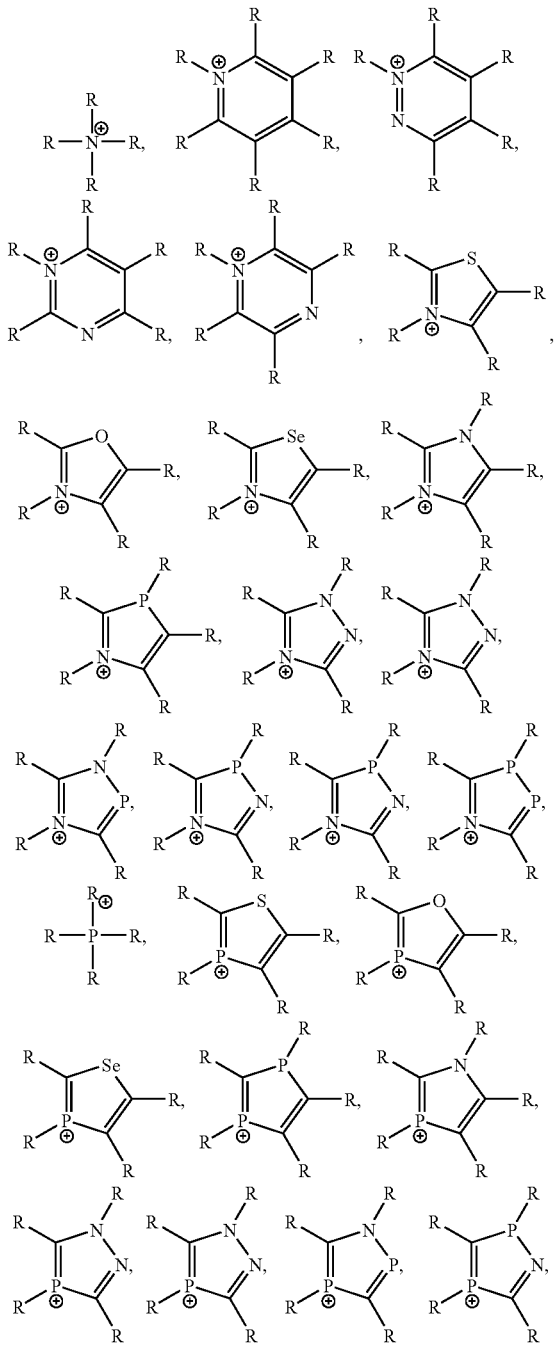

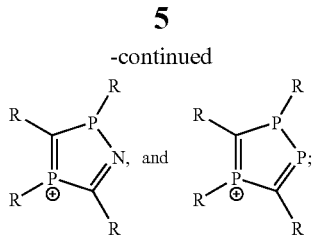

provided that at least one Z is selected from the group consisting of R

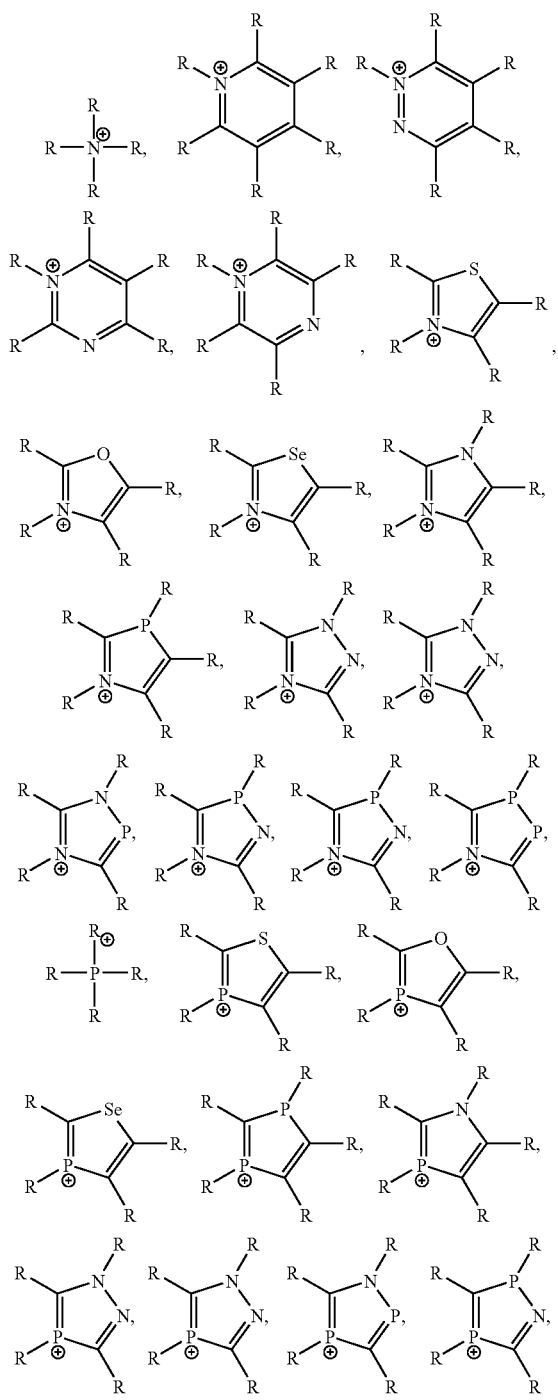

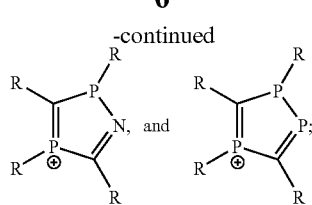

R is a bond to W or is selected, independently for each occurrence, from the group consisting of hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano;

provided that exactly one R is a bond to W; and any two adjacent R, taken together with the atoms to which they are directly bound, may form a 5-membered, 6-membered, or 7-membered, saturated or unsaturated, carbocyclic or heterocyclic, ring.

In certain embodiments, the present invention relates to the aforementioned salt, wherein said anionic component is Y.

In certain embodiments, the present invention relates to the aforementioned salt, wherein Y is selected from the group consisting of $[CH_3CO_2]^{-1}$, $[Cl]^{-1}$, $[ClO_4]^{-1}$, $[Br]^{-1}$, $[I]^{-1}$, $[SO_4]^{-2}$, $[CH_3SO_3]^{-1}$, $[SbF_6]^{-1}$, $[N(CN)_2]^{-1}$, $[CF_3S(O)_2NS(O)_2CF_3]^{-1}$, $[PF_6]^{-1}$, $[BF_4]^{-1}$, $[B(CN)_4]^{-1}$, $[AlCl_4]^{-1}$, $[Al_2Cl_7]^{-1}$, $[CuCl_2]^{-1}$, $[Cu_2Cl_3]^{-1}$, $[ZnCl_3]^{-1}$, $[ZnCl_4]^{-2}$, $[Zn_2Cl_5]^{-1}$, $[FeCl_3]^{-1}$, $[FeCl_4]^{-1}$, $[Fe_2Cl_7]^{1}$, $[TiCl_5]^{1}$, $[TiCl_6]^{-2}$, $[SnCl_3]^{-1}$, $[SnCl_5]^{-1}$, $[SnCl_6]^{-2}$, and $[CrCl_4]^{-1}$.

In certain embodiments, the present invention relates to the aforementioned salt, wherein said anionic component is $X—[Y]_m$.

In certain embodiments, the present invention relates to the aforementioned salt, wherein Y is selected, independently for each occurrence, from the group consisting of $—[CO_2]^{-1}$, $—[SO_3]^{-1}$, $—[SO_4]^{-2}$, $—[SbF_5]^{-1}$, $—[N(CN)]^{-1}$, $—[CF_2S(O)_2NS(O)_2CF_3]^{-1}$, $—[PF_5]^{-1}$, $—[B(CN)_3]^{-1}$, and $—[BF_3]^{-1}$.

In certain embodiments, the present invention relates to the aforementioned salt, wherein Y is $—[CO_2]^{-1}$.

In certain embodiments, the present invention relates to the aforementioned salt, wherein m is 2-20 inclusive.

In certain embodiments, the present invention relates to the aforementioned salt, wherein m is 2-10 inclusive In certain embodiments, the present invention relates to the aforementioned salt, where m is 2, 3 or 4.

In certain embodiments, the present invention relates to the aforementioned salt, wherein X is selected, independently for each occurrence, from the group consisting of linear or branched alkanes, linear or branched polyethylene glycols, linear or branched poly(propylene glycol), linear or branched polyethers, linear or branched polyacrylic acids, linear or branched polyamides, and polyether triamines, or a combination thereof.

In certain embodiments, the present invention relates to the aforementioned salt, wherein X is -A-, -AO(AO)$_p$A-, or -ANH(ANH)$_p$A-; A is, independently for each occurrence, $—(CQ_2)_p—$; Q is, independently for each occurrence, hydrogen or methyl; and p is, independently for each occurrence, 0-40 inclusive.

In certain embodiments, the present invention relates to the aforementioned salt, wherein X is C(R')(A-)$_3$, C(R')[(AO)$_p$A-]$_3$, C(R')[(ANH)$_p$A-]$_3$, N(A-)$_3$, N[(AO)$_p$A-]$_3$, or N[(ANH)$_p$A-]$_3$; A is, independently for each occurrence, —(CQ$_2$)$_p$-; Q is, independently for each occurrence, hydrogen or methyl; p is, independently for each occurrence, 0-40 inclusive; and R' is hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano.

In certain embodiments, the present invention relates to the aforementioned salt, wherein X is C(ACH$_2$—)$_4$, C[(AO)$_p$A-]$_4$, C[(ANH)$_p$A-]$_4$, (-A)$_2$N(AO)$_p$AN(A-)$_2$, or (-A)$_2$N(ANH)$_p$AN(A-)$_2$; A is, independently for each occurrence, —(CQ$_2$)$_p$-; Q is, independently for each occurrence, hydrogen or methyl; and p is, independently for each occurrence, 0-40 inclusive.

In certain embodiments, the present invention relates to the aforementioned salt, wherein W is selected, independently for each occurrence, from the group consisting of linear or branched alkanes, linear or branched polyethylene glycols, linear or branched poly(propylene glycol), linear or branched polyethers, linear or branched polyacrylic acids, linear or branched polyamides, polyether triamines, or a combination thereof.

In certain embodiments, the present invention relates to the aforementioned salt, wherein W is -A-, -AO(AO)$_p$A-, or -ANH(ANH)$_p$A-; A is, independently for each occurrence, —(CQ$_2$)$_p$-; Q is, independently for each occurrence, hydrogen or methyl; and p is, independently for each occurrence, 0-40 inclusive.

In certain embodiments, the present invention relates to the aforementioned salt, wherein W is C(R')(A-)$_3$, C(R')[(AO)$_p$A-]$_3$, C(R')[(ANH)$_p$A-]$_3$, N(A-)$_3$, N[(AO)$_p$A-]$_3$, or N[(ANH)$_p$A-]$_3$; A is, independently for each occurrence, —(CQ$_2$)$_p$-; Q is, independently for each occurrence, hydrogen or methyl; p is, independently for each occurrence, 0-40 inclusive; and R' is hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano.

In certain embodiments, the present invention relates to the aforementioned salt, wherein W is C(ACH$_2$—)$_4$, C[(AO)$_p$A-]$_4$, C[(ANH)$_p$A-]$_4$, (-A)$_2$N(AO)$_p$AN(A-)$_2$, or (-A)$_2$N(ANH)$_p$AN(A-)$_2$; A is, independently for each occurrence, —(CQ$_2$)$_p$-; Q is, independently for each occurrence, hydrogen or methyl; and p is, independently for each occurrence, 0-40 inclusive.

In certain embodiments, the present invention relates to the aforementioned salt, wherein X and W are the same.

In certain embodiments, the present invention relates to the aforementioned salt, wherein n is 2-20 inclusive.

In certain embodiments, the present invention relates to the aforementioned salt, wherein n is 2-10 inclusive In certain embodiments, the present invention relates to the aforementioned salt, where n is 2, 3, or 4.

In certain embodiments, the present invention relates to the aforementioned salt, wherein Z is selected, independently for each occurrence, from the group consisting of

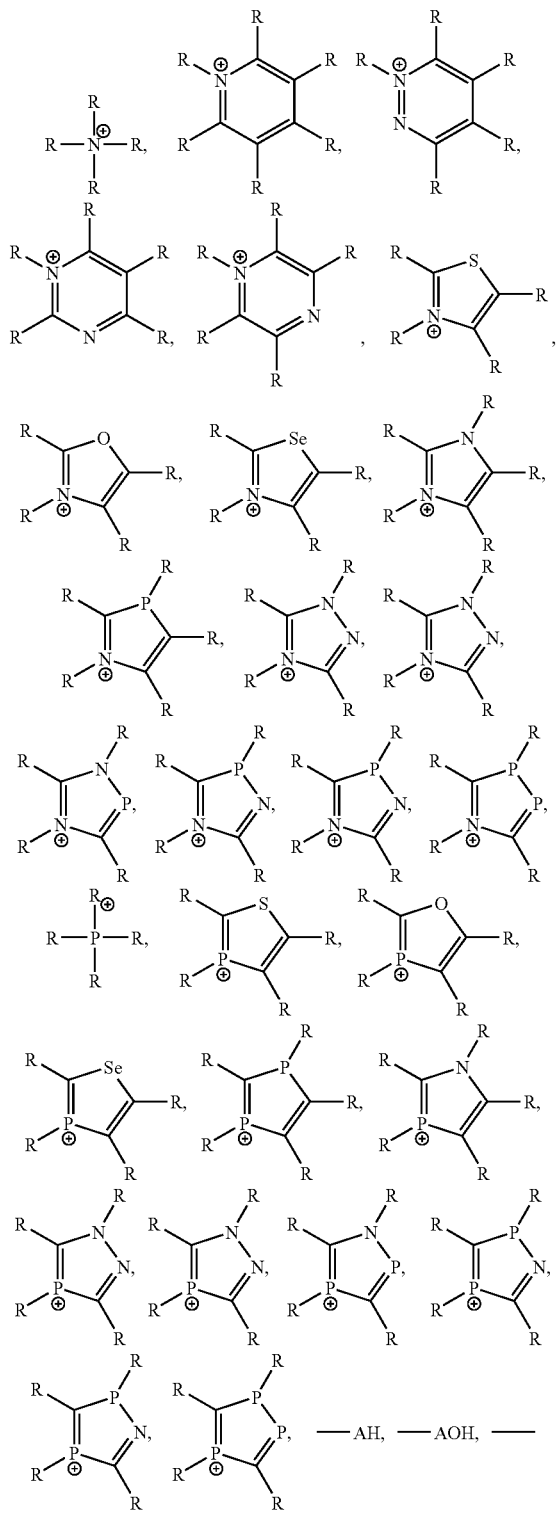

CH(OAH)(AOH), -(p-AH)Ph, and —Si(OH)(AH)A is, independently for each occurrence, —(CQ$_2$)$_p$-; Q is, independently for each occurrence, hydrogen or methyl; and r is, independently for each occurrence, 0-40 inclusive.

In certain embodiments, the present invention relates to the aforementioned salt, wherein Z is selected, independently for each occurrence, from the group consisting of

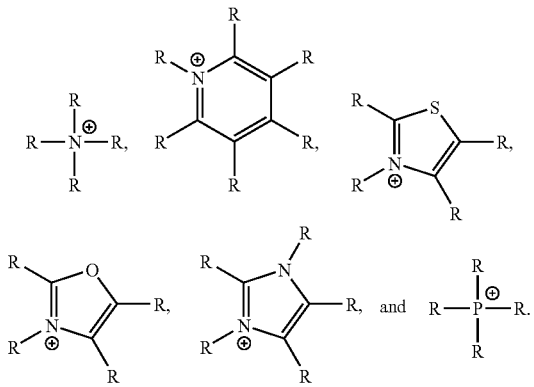

In certain embodiments, the present invention relates to the aforementioned salt, wherein R is a bond to W or is selected, independently for each occurrence, from the group consisting of hydrogen or alkyl.

In certain embodiments, the present invention relates to the aforementioned salt, wherein at least one Z is selected from the group consisting of halogen, azide, aralkyl, alkenyl, alkynyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, and cyano.

Another aspect of the invention relates to a salt comprising an anionic component and a cationic component, wherein:

said anionic component is X—[Y]$_2$, X—[Y]$_3$, or X—[Y]$_4$;

X is selected from the group consisting of linear or branched alkanes, linear or branched alkenes, linear or branched alkynes, monocyclic or polycyclic aromatics, monocyclic or polycyclic heteroaromatics, linear or branched polysilanes, linear or branched polyethylene glycols, linear or branched poly(propylene glycol), linear or branched polyalkylene oxides, linear or branched polysiloxanes, linear or branched polyacrylates, linear or branched polyacetals, linear or branched acrylics, linear or branched cellulosics, linear or branched polyethers, linear or branched halogenated polyethers, linear or branched halocarbons, linear or branched polyamides, linear or branched polycarbonates, linear or branched polyethylenes, linear or branched polypropylenes, linear or branched polystyrenes, and linear or branched polyurethanes, or a combination thereof;

Y is selected, independently for each occurrence, from the group consisting of carboxylic acids, sulfonic acids, tetrafluoroborates, hexafluorophosphates, bis-trifluoromethane-sulfonimides, borates, phosphates, nitrates, sulfates, triflates, antimonates, phosphoniums, carboranes, polyoxo metallates, and metalloboranes;

said cationic component is W—[Z]$_2$, W—[Z]$_3$, or W—[Z]$_4$;

W is absent, or selected from the group consisting of linear or branched alkanes, linear or branched alkenes, linear or branched alkynes, monocyclic or polycyclic aromatics, monocyclic or polycyclic heteroaromatics, linear or branched polysilanes, linear or branched polyethylene glycols, linear or branched poly(propylene glycol), linear or branched polyalkylene oxides, linear or branched polysiloxanes, linear or branched polyacrylates, linear or branched polyacetals, linear or branched acrylics, linear or branched cellulosics, linear or branched polyethers, linear or branched halogenated polyethers, linear or branched halocarbons, linear or branched polyamides, linear or branched polycarbonates, linear or branched polyethylenes, linear or branched polypropylenes, linear or branched polystyrenes, and linear or branched polyurethanes, or a combination thereof;

Z is selected, independently for each occurrence, from the group consisting of hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, cyano,

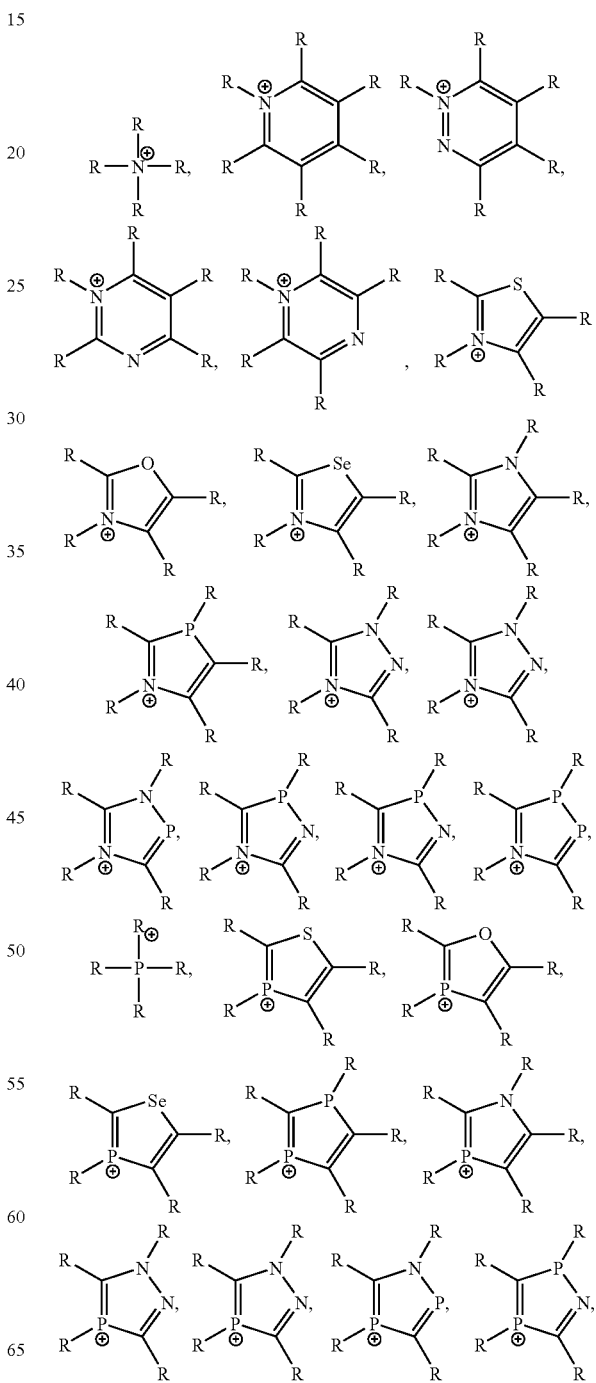

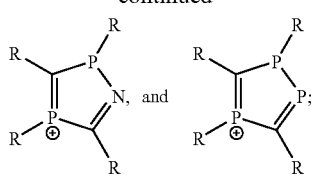

provided that at least one Z is selected from the group consisting of

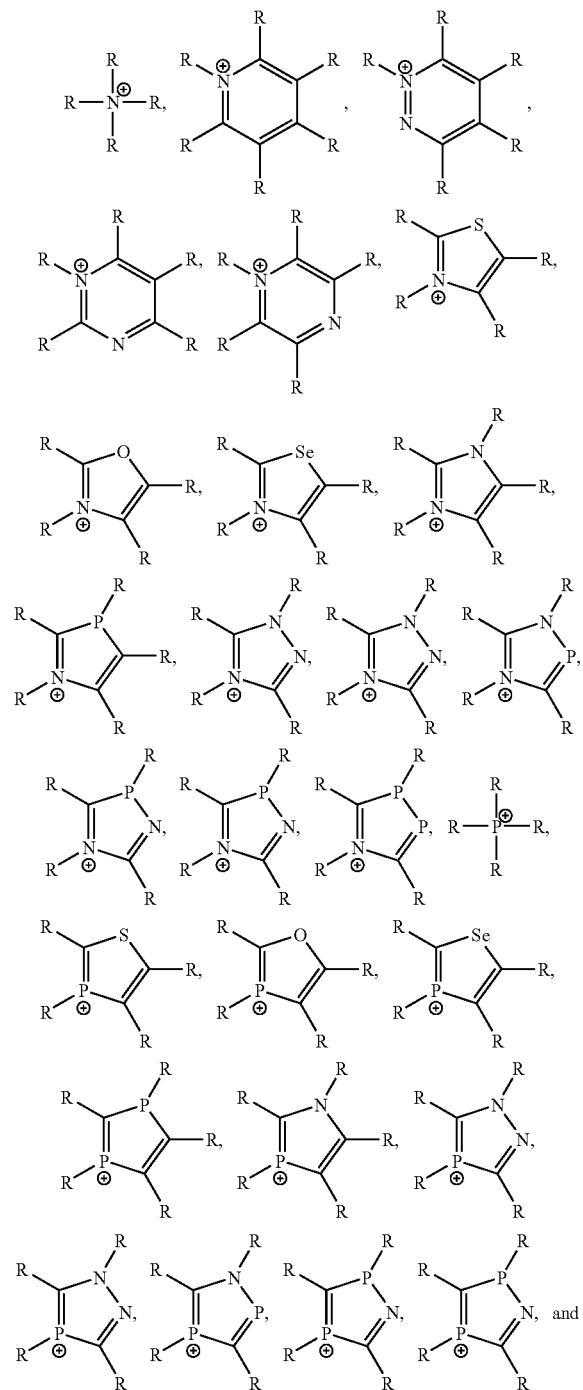

R is a bond to W or is selected, independently for each occurrence, from the group consisting of hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano; and provided that for every Z exactly one R is a bond to W.

In certain embodiments, the present invention relates to the aforementioned salt, wherein Y is selected, independently for each occurrence, from the group consisting of $-[CO_2]^{-1}$, $-[SO_3]^{-1}$, $-[SO_4]^{-2}$, $-[SbF_5]^{-1}$, $-[N(CN)]^{-1}$, $-[CF_2S(O)_2NS(O)_2CF_3]^{-1}$, $-[PF_5]^{-1}$, $-[B(CN)_3]^{-1}$, and $-[BF_3]^{-1}$.

In certain embodiments, the present invention relates to the aforementioned salt, wherein Y is $-[CO_2]^{-1}$.

In certain embodiments, the present invention relates to the aforementioned salt, wherein X is selected, independently for each occurrence, from the group consisting of linear or branched alkanes, linear or branched poly(ethylene glycol), linear or branched poly(propylene glycol), linear or branched polyethers, linear or branched polyacrylic acids, linear or branched polyamines, polyether polyamines, or a combination thereof.

In certain embodiments, the present invention relates to the aforementioned salt, wherein W is selected, independently for each occurrence, from the group consisting of linear or branched alkanes, linear or branched poly(ethylene glycol), linear or branched poly(propylene glycol), linear or branched polyethers, linear or branched polyacrylic acids, linear or branched polyamides, polyether polyamines, or a combination thereof.

In certain embodiments, the present invention relates to the aforementioned salt, wherein Z is selected, independently for each occurrence, from the group consisting of

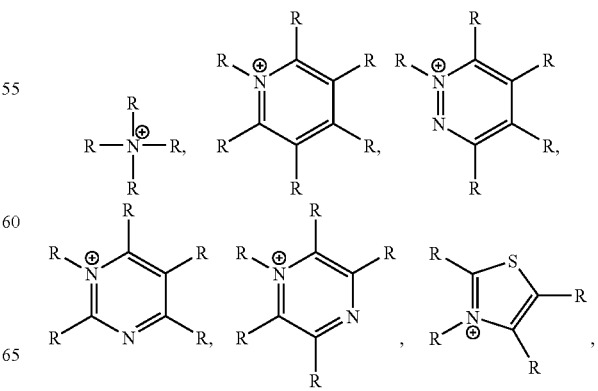

-continued
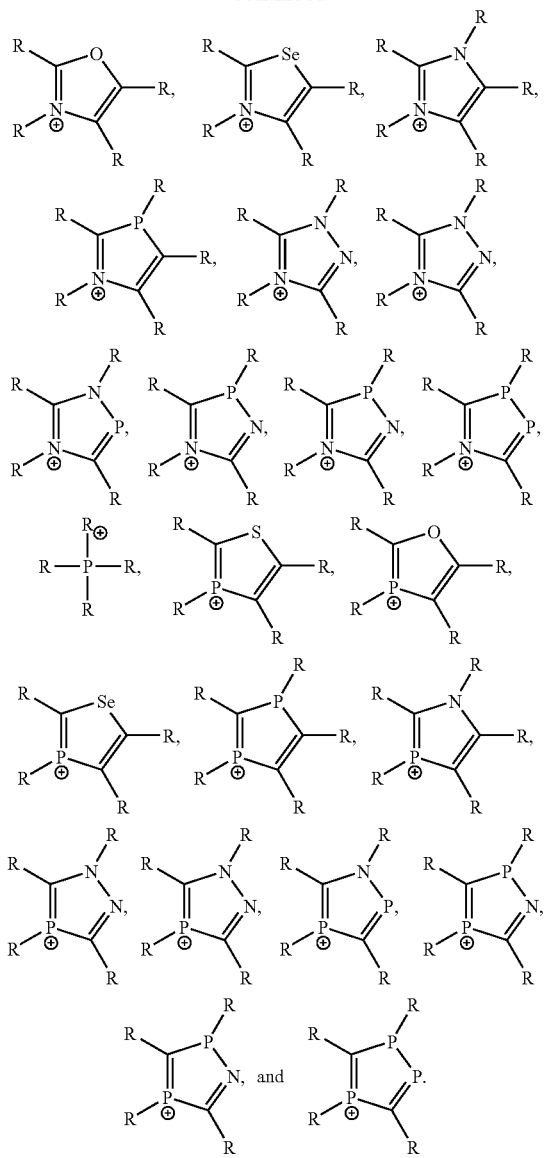
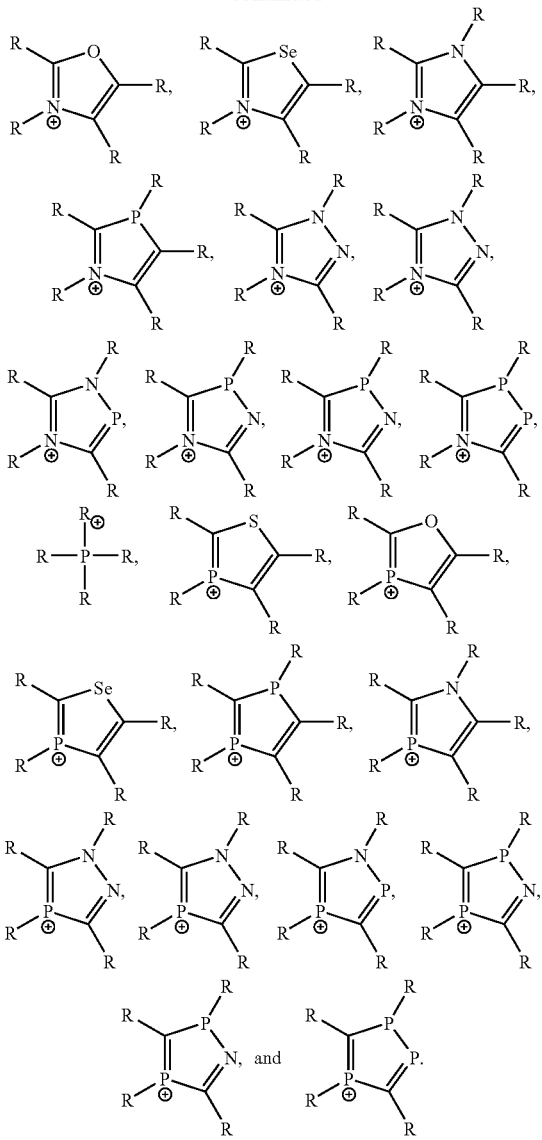
In certain embodiments, the present invention relates to the aforementioned salt, wherein Z is selected from the group consisting of
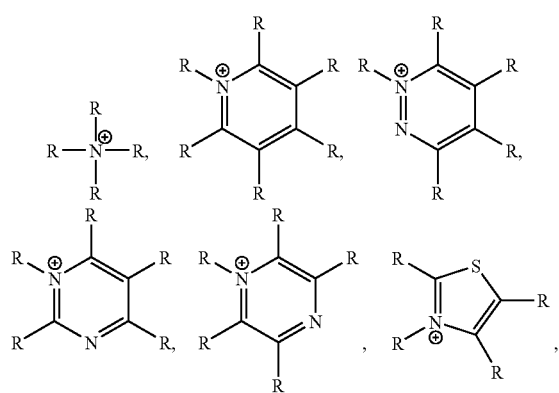
In certain embodiments, the present invention relates to the aforementioned salt, wherein Z is selected, independently for each occurrence, from the group consisting of
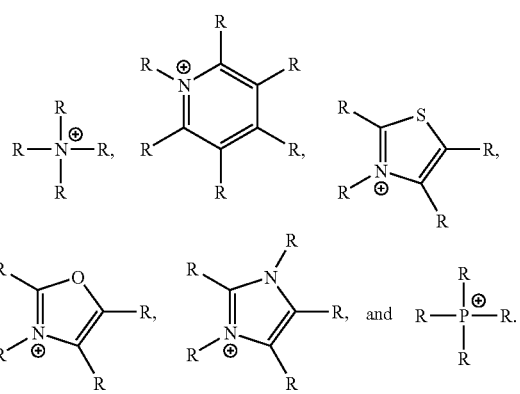

In certain embodiments, the present invention relates to the aforementioned salt, wherein Z is selected from the group consisting of

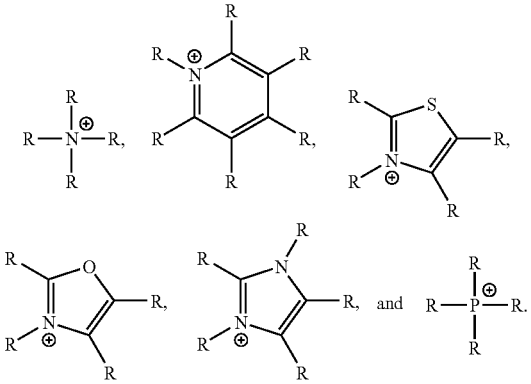

In certain embodiments, the present invention relates to the aforementioned salt, wherein Z is —N(R)₃ or —P(R)₃.

In certain embodiments, the present invention relates to the aforementioned salt, wherein Z is —NH₃.

In certain embodiments, the present invention relates to the aforementioned salt, wherein Z is —P(R")₃; and R" is, independently for each occurrence, hydrogen, alkyl, aryl, or aralkyl.

In certain embodiments, the present invention relates to the aforementioned salt, wherein Z is —P(CH₂CH₂CH₂CH₂CH₃)₃.

In certain embodiments, the present invention relates to the aforementioned salt, wherein at least one Z is

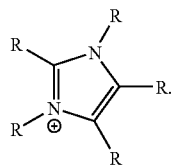

In certain embodiments, the present invention relates to the aforementioned salt, wherein Z is

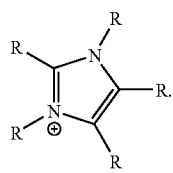

In certain embodiments, the present invention relates to the aforementioned salt, wherein at least one Z is

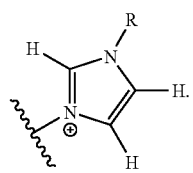

In certain embodiments, the present invention relates to the aforementioned salt, wherein Z is

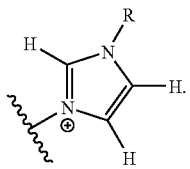

In certain embodiments, the present invention relates to the aforementioned salt, wherein at least one Z is

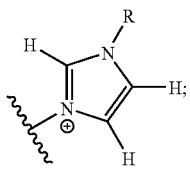

and R is alkyl.

In certain embodiments, the present invention relates to the aforementioned salt, wherein Z is

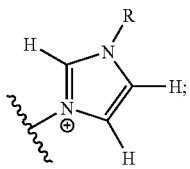

and R is alkyl.

In certain embodiments, the present invention relates to the aforementioned salt, wherein at least one Z is

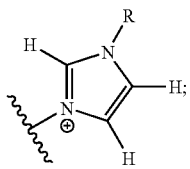

and R is —CH₃, —CH₂CH₃, —CH₂CH₂CH₃, —CH₂CH₂CH₂CH₃, or —CH₂CH₂CH₂CH₂CH₃.

In certain embodiments, the present invention relates to the aforementioned salt, wherein Z is

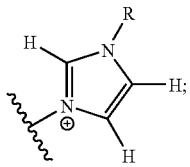

and R is —CH₃, —CH₂CH₃, —CH₂CH₂CH₂CH₃, or —CH₂CH₂CH₂CH₂CH₃.

In certain embodiments, the present invention relates to the aforementioned salt, wherein at least one occurrence of Z is -AH, -AOH, —CH(OAH)(AOH), -(p-AH)Ph, and —Si(OH)

(AH); A is, independently for each occurrence, —$(CQ_2)_p$-; Q is, independently for each occurrence, hydrogen or methyl; and r is, independently for each occurrence, 0-40 inclusive.

In certain embodiments, the present invention relates to the aforementioned salt, wherein at least one occurrence of Z is -AH, -AOH, —CH(OAH)(AOH), -(p-AH)Ph, and —Si(OH)(AH); A is, independently for each occurrence, —$(CQ_2)_p$-; Q is, independently for each occurrence, hydrogen or methyl; r is, independently for each occurrence, 0-40 inclusive; and W is absent.

In certain embodiments, the present invention relates to the aforementioned salt, wherein at least one occurrence of Z is —$CH_2CH_3$, —$CH_2CH_2OH$, —$CH(OCH_2CH_3)(CH_2OH)$, -(p-$CH_2CH_2$)Ph, and —Si(OH)($CH_3$).

In certain embodiments, the present invention relates to the aforementioned salt, wherein at least one occurrence of Z is —$CH_2CH_3$, —$CH_2CH_2OH$, —$CH(OCH_2CH_3)(CH_2OH)$, -(p-$CH_2CH_2$)Ph, and —Si(OH)($CH_3$); and W is absent.

In certain embodiments, the present invention relates to the aforementioned salt, wherein at least one R is —$(C(J)_2)_nCJ_3$; J is selected, independently for each occurrence, from the group consisting of —H, —F, —Cl, —N($C_1$-$C_{10}$ fluoroalkyl)$_2$, —N($C_1$-$C_{10}$ fluoroalkyl)($C_1$-$C_{10}$ alkyl), —O($C_1$-$C_{10}$ fluoroalkyl), —$SO_2$($C_1$-$C_{10}$ fluoroalkyl), or —$C_1$-$C_{10}$ fluoroalkyl; and s is 0-40 inclusive.

In certain embodiments, the present invention relates to the aforementioned salt, wherein R is a bond to W or is selected, independently for each occurrence, from the group consisting of hydrogen or alkyl.

In certain embodiments, the present invention relates to the aforementioned salt, wherein said cationic component is W—$[Z]_2$.

In certain embodiments, the present invention relates to the aforementioned salt, wherein said anionic component is X—$[Y]_2$; X is -A-, -AO(AO)$_q$A-, -ANH(ANH)$_q$A-; A is, independently for each occurrence, —$(CQ_2)_p$-; Q is, independently for each occurrence, hydrogen or methyl; and p is, independently for each occurrence, 0-40 inclusive.

In certain embodiments, the present invention relates to the aforementioned salt, wherein A is absent, or selected, independently for each occurrence, from the group consisting of —$CH_2$—, —$CH_2CH_2$—, —$CH_2CH_2CH_2$—, —$CH_2CH_2CH_2CH_2$—, and —$CH_2CH_2CH_2CH_2CH_2$—

In certain embodiments, the present invention relates to the aforementioned salt, wherein said anionic component is X—$[Y]_2$; X is —$(CH_2)_q$—, —$CH_2$—O—$(CH_2O)_qCH_2$—, —$CH_2$—O—$(CH_2CH_2O)_qCH_2$—, —$CH_2CH_2$—O—$(CH_2CH_2CH_2O)_qCH_2CH_2$—, —$CH_2CH_2CH_2$—O—$(CH_2CH_2CH_2CH_2O)_qCH_2CH_2CH_2$—, —$CH_2NH$($CH_2NH)_qCH_2$—, $CH_2CH_2NH(CH_2CH_2CH_2NH)_qCH_2CH_2$—, or —$CH_2CH_2CH_2NH(CH_2CH_2CH_2CH_2NH)_qCH_2CH_2CH_2$—; and q is 0-40 inclusive.

In certain embodiments, the present invention relates to the aforementioned salt, wherein said anionic component is X—$[Y]_2$; X is —$CH_2OCH_2CH_2OCH_2$—, —$(CH_2)_{10}$—, or poly(acrylonitrile-co-butadiene).

In certain embodiments, the present invention relates to the aforementioned salt, wherein said anionic component is X—$[Y]_3$; X is C(R')(A-)$_3$, C(R')[(AO)$_p$A-]$_3$, C(R')[(ANH)$_p$A-]$_3$, N(A)$_3$, N[(AO)$_p$A-]$_3$, or N[(ANH)$_p$A-]$_3$; A is, independently for each occurrence, —$(CQ_2)_p$-; Q is, independently for each occurrence, hydrogen or methyl; p is, independently for each occurrence, 0-40 inclusive; and R' is hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano.

In certain embodiments, the present invention relates to the aforementioned salt, wherein said anionic component is X—$[Y]_3$; X is C(R')(A-)$_3$, C(R')[(AO)$_p$A-]$_3$, or C(R')[(ANH)$_p$ A-]$_3$; A is, independently for each occurrence, —$(CQ_2)_p$-; Q is, independently for each occurrence, hydrogen or methyl; p is, independently for each occurrence, 0-10 inclusive; and R' is hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano.

In certain embodiments, the present invention relates to the aforementioned salt, wherein said anionic component is X—$[Y]_3$; X is N(A)$_3$, N[(AO)$_p$A-]$_3$, or N[(ANH)$_p$A-]$_3$; A is, independently for each occurrence, —$(CQ_2)_p$-; Q is, independently for each occurrence, hydrogen or methyl; and p is, independently for each occurrence, 0-10 inclusive.

In certain embodiments, the present invention relates to the aforementioned salt, wherein A is absent, or selected, independently for each occurrence, from the group consisting of —$CH_2$—, —$CH_2CH_2$—, —$CH_2CH_2CH_2$—, —$CH_2CH_2CH_2CH_2$—, and —$CH_2CH_2CH_2CH_2CH_2$—

In certain embodiments, the present invention relates to the aforementioned salt, wherein said anionic component is X—$[Y]_4$; X is C($ACH_2$—)$_4$, C[(AO)$_p$A-]$_4$, C[(ANH)$_p$A-]$_4$, (-A)$_2$N(AO)$_p$AN(A-)$_2$, or (-A)$_2$N(ANH)$_p$AN(A-)$_2$; A is, independently for each occurrence, —$(CQ_2)_p$-; Q is, independently for each occurrence, hydrogen or methyl; and p is, independently for each occurrence, 0-40 inclusive.

In certain embodiments, the present invention relates to the aforementioned salt, wherein A is absent, or selected, independently for each occurrence, from the group consisting of —$CH_2$—, —$CH_2CH_2$—, —$CH_2CH_2CH_2$—, —$CH_2CH_2CH_2CH_2$—, and —$CH_2CH_2CH_2CH_2CH_2$—.

In certain embodiments, the present invention relates to the aforementioned salt, wherein W is -A-, -AO(AO)$_q$A-, -ANH(ANH)$_q$A-; A is, independently for each occurrence, —$(CQ_2)_p$-; Q is, independently for each occurrence, hydrogen or methyl; and q is, independently for each occurrence, 0-40 inclusive.

In certain embodiments, the present invention relates to the aforementioned salt, wherein W is —$(CH_2)_q$—, —$CH_2O$($CH_2O)_qCH_2$—, —$CH_2O(CH_2CH_2O)_qCH_2$—, —$CH_2CH_2$—O—$(CH_2CH_2CH_2O)_qCH_2CH_2$—, —$CH_2CH_2CH_2O(CH_2CH_2CH_2CH_2O)_qCH_2CH_2CH_2$—, —$CH_2NH(CH_2NH)_qCH_2$—, —$CH_2NH(CH_2CH_2NH)_qCH_2$—, —$CH_2CH_2NH(CH_2CH_2CH_2NH)_qCH_2CH_2$—, or —$CH_2CH_2CH_2NH(CH_2CH_2CH_2CH_2NH)_qCH_2CH_2CH_2$—; and q is 0-40 inclusive.

In certain embodiments, the present invention relates to the aforementioned salt, wherein W is —$CH_2CH_2OCH_2CH_2OCH_2CH_2$—, —$(CH_2)_{10}$—, or poly(acrylonitrile-co-butadiene).

In certain embodiments, the present invention relates to the aforementioned salt, wherein W—$[Z]_2$ is [Z]-W—[N(R")$_3$] or [Z]-W—[P(R")$_3$]; R" is, independently for each occurrence, hydrogen, alkyl, aryl, or aralkyl.

In certain embodiments, the present invention relates to the aforementioned salt, wherein W—$[Z]_2$ is [N(R")$_3$]-W—[N(R")$_3$] or [P(R")$_3$]—W—[P(R")$_3$]; and R" is hydrogen, alkyl, aryl, or aralkyl.

In certain embodiments, the present invention relates to the aforementioned salt, wherein W—[Z]$_2$ is [NH$_3$]—W—[NH$_3$].

In certain embodiments, the present invention relates to the aforementioned salt, wherein W—[Z]$_2$ is [P(CH$_2$CH$_2$CH$_2$CH$_2$CH$_3$)$_3$]—W—[P(CH$_2$CH$_2$CH$_2$CH$_2$CH$_2$CH$_3$)$_3$].

In certain embodiments, the present invention relates to the aforementioned salt, wherein at least one Z is

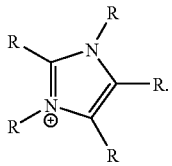

In certain embodiments, the present invention relates to the aforementioned salt, wherein Z is

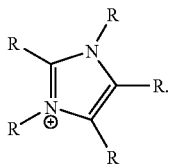

In certain embodiments, the present invention relates to the aforementioned salt, wherein at least one Z is

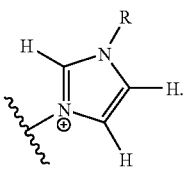

In certain embodiments, the present invention relates to the aforementioned salt, wherein Z is

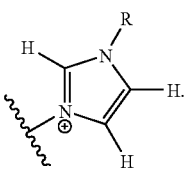

In certain embodiments, the present invention relates to the aforementioned salt, wherein at least one Z is

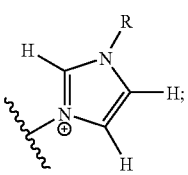

and R is alkyl.

In certain embodiments, the present invention relates to the aforementioned salt, wherein Z is

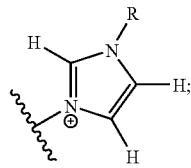

and R is alkyl.

In certain embodiments, the present invention relates to the aforementioned salt, wherein at least one Z is

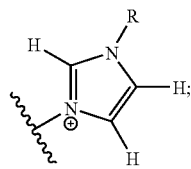

and R is —CH$_3$, —CH$_2$CH$_3$, —CH$_2$CH$_2$CH$_3$, —CH$_2$CH$_2$CH$_2$CH$_3$, or —CH$_2$CH$_2$CH$_2$CH$_2$CH$_3$.

In certain embodiments, the present invention relates to the aforementioned salt, wherein Z is

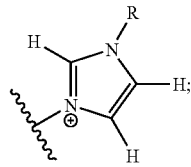

and R is —CH$_3$, —CH$_2$CH$_3$, —CH$_2$CH$_2$CH$_3$, —CH$_2$CH$_2$CH$_2$CH$_3$, or —CH$_2$CH$_2$CH$_2$CH$_2$CH$_3$.

In certain embodiments, the present invention relates to the aforementioned salt, wherein W—[Z]$_2$ is [D]-W—[Z]; and D is selected from the group consisting of -AH, -AOH, —CH(OAH)(AOH), -(p-AH)Ph, and —Si(OH)(AH); A is, independently for each occurrence, —(CQ$_2$)$_p$-; Q is, independently for each occurrence, hydrogen or methyl; and r is, independently for each occurrence, 0-40 inclusive.

In certain embodiments, the present invention relates to the aforementioned salt, wherein W—[Z]$_2$ is [D]-W—[Z]; and D is selected from the group consisting of —CH$_2$CH$_3$, —CH$_2$CH$_2$OH, —CH(OCH$_2$CH$_3$)(CH$_2$OH), -(p-CH$_2$CH$_2$)Ph, and —Si(OH)(CH$_3$).

In certain embodiments, the present invention relates to the aforementioned salt, wherein W—[Z]$_2$ is [D]-[Z]; and D is selected from the group consisting of -AH, -AOH, —CH(OAH)(AOH), -(p-AH)Ph, and —Si(OH)(AH); A is, independently for each occurrence, —(CQ$_2$)$_p$-; Q is, independently for each occurrence, hydrogen or methyl; and r is, independently for each occurrence, 0-40 inclusive.

In certain embodiments, the present invention relates to the aforementioned salt, wherein W—[Z]$_2$ is [D]-[Z]; and D is selected from the group consisting of —CH$_2$CH$_3$, —CH$_2$CH$_2$OH, —CH(OCH$_2$CH$_3$)(CH$_2$OH), -(β-CH$_2$CH$_2$)Ph, and —Si(OH)(CH$_3$).

In certain embodiments, the present invention relates to the aforementioned salt, wherein said cationic component is W—[Z]$_3$.

In certain embodiments, the present invention relates to the aforementioned salt, wherein said anionic component is X—[Y]$_2$; X is -A-, -AO(AO)$_q$A-, -ANH(ANH)$_q$A-; A is, independently for each occurrence, —(CQ$_2$)$_p$-; Q is, independently for each occurrence, hydrogen or methyl; and p is, independently for each occurrence, 0-40 inclusive.

In certain embodiments, the present invention relates to the aforementioned salt, wherein A is absent, or selected, independently for each occurrence, from the group consisting of —CH$_2$—, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

In certain embodiments, the present invention relates to the aforementioned salt, wherein said anionic component is X—[Y]$_2$; X is —(CH$_2$)$_q$—, —CH$_2$—O—(CH$_2$O)$_q$CH$_2$—, —CH$_2$—O—(CH$_2$CH$_2$O)$_q$CH$_2$—, —CH$_2$CH$_2$—O—(CH$_2$CH$_2$CH$_2$O)$_q$CH$_2$CH$_2$—, —CH$_2$CH$_2$CH$_2$O(CH$_2$CH$_2$CH$_2$CH$_2$O)$_q$CH$_2$CH$_2$CH$_2$—, —CH$_2$NH(CH$_2$NH)$_q$CH$_2$—, —CH$_2$NH(CH$_2$CH$_2$NH)$_q$CH$_2$—, —CH$_2$CH$_2$NH(CH$_2$CH$_2$CH$_2$NH)$_q$CH$_2$CH$_2$—, or —CH$_2$CH$_2$CH$_2$NH(CH$_2$CH$_2$CH$_2$CH$_2$NH)$_q$CH$_2$CH$_2$CH$_2$—; and q is 0-40 inclusive.

In certain embodiments, the present invention relates to the aforementioned salt, wherein said anionic component is X—[Y]$_2$; X is —CH$_2$OCH$_2$CH$_2$OCH$_2$—, —(CH$_2$)$_{10}$—, or poly(acrylonitrile-co-butadiene).

In certain embodiments, the present invention relates to the aforementioned salt, wherein said anionic component is X—[Y]$_3$; X is C(R')(A-)$_3$, C(R')[(AO)$_p$A-]$_3$, C(R')[(ANH)$_p$A-]$_3$, N(A)$_3$, N[(AO)$_p$A-]$_3$, or N[(ANH)$_p$A-]$_3$; A is, independently for each occurrence, —(CQ$_2$)$_p$-; Q is, independently for each occurrence, hydrogen or methyl; p is, independently for each occurrence, 0-40 inclusive; and R' is hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano.

In certain embodiments, the present invention relates to the aforementioned salt, wherein said anionic component is X—[Y]$_3$; X is C(R')(A-)$_3$, C(R')[(AO)$_p$A-]$_3$, or C(R')[(ANH)$_p$ A-]$_3$; A is, independently for each occurrence, —(CQ$_2$)$_p$-; Q is, independently for each occurrence, hydrogen or methyl; p is, independently for each occurrence, 0-10 inclusive; and R' is hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano.

In certain embodiments, the present invention relates to the aforementioned salt, wherein said anionic component is X—[Y]$_3$; X is N(A)$_3$, N[(AO)$_p$A-]$_3$, or N[(ANH)$_p$A-]$_3$; A is, independently for each occurrence, —(CQ$_2$)$_p$-; Q is, independently for each occurrence, hydrogen or methyl; and p is, independently for each occurrence, 0-10 inclusive.

In certain embodiments, the present invention relates to the aforementioned salt, wherein A is absent, or selected, independently for each occurrence, from the group consisting of —CH$_2$—, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

In certain embodiments, the present invention relates to the aforementioned salt, wherein said anionic component is X—[Y]$_4$; X is C(ACH$_2$—)$_4$, C[(AO)$_p$A-]$_4$, C[(ANH)$_p$A-]$_4$, (-A)$_2$N(AO)$_p$AN(A-)$_2$, or (-A)$_2$N(ANH)$_p$AN(A-)$_2$; A is, independently for each occurrence, —(CQ$_2$)$_p$-; Q is, independently for each occurrence, hydrogen or methyl; and p is, independently for each occurrence, 0-40 inclusive.

In certain embodiments, the present invention relates to the aforementioned salt, wherein A is absent, or selected, independently for each occurrence, from the group consisting of —CH$_2$—, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

In certain embodiments, the present invention relates to the aforementioned salt, wherein W is C(R')(A-)$_3$, C(R')[(AO)$_p$A-]$_3$, C(R')[(ANH)$_p$A-]$_3$, N(A)$_3$, N[(AO)$_p$A-]$_3$, or N[(ANH)$_p$A-]$_3$; A is, independently for each occurrence, —(CQ$_2$)$_p$-; Q is, independently for each occurrence, hydrogen or methyl; p is, independently for each occurrence, 0-40 inclusive; and R' is hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano.

In certain embodiments, the present invention relates to the aforementioned salt, wherein W is C(R')(A-)$_3$, C(R')[(AO)$_p$A-]$_3$, or N(A-)$_3$; A is, independently for each occurrence, —(CQ$_2$)$_p$-; Q is, independently for each occurrence, hydrogen or methyl; p is, independently for each occurrence, 0-40 inclusive; and R' is hydrogen or alkyl.

In certain embodiments, the present invention relates to the aforementioned salt, wherein W is C(R')(A-)$_3$, C(R')[(AO)$_p$A-]$_3$, or N(A-)$_3$; A is, independently for each occurrence, —(CQ$_2$)$_p$-; Q is, independently for each occurrence, hydrogen or methyl; p is, independently for each occurrence, 0-40 inclusive; and R' is hydrogen or methyl.

In certain embodiments, the present invention relates to the aforementioned salt, wherein W—[Z]$_3$ is [Z]$_2$—W—[N(R")$_3$] or [Z]$_2$—W—[P(R")$_3$]; R" is, independently for each occurrence, hydrogen, alkyl, aryl, or aralkyl.

In certain embodiments, the present invention relates to the aforementioned salt, wherein W—[Z]$_3$ is [Z]-W—[N(R")$_3$]$_2$ or [Z]-W—[P(R")$_3$]$_2$; and R" is hydrogen, alkyl, aryl, or aralkyl.

In certain embodiments, the present invention relates to the aforementioned salt, wherein W—[Z]$_3$ is W—[NH$_3$]$_3$.

In certain embodiments, the present invention relates to the aforementioned salt, wherein W—[Z]$_3$ is W—[P(CH$_2$CH$_2$CH$_2$CH$_3$)$_3$]$_3$.

In certain embodiments, the present invention relates to the aforementioned salt, wherein at least one Z is

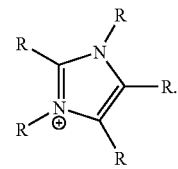

In certain embodiments, the present invention relates to the aforementioned salt, wherein Z is

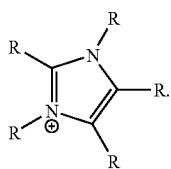

In certain embodiments, the present invention relates to the aforementioned salt, wherein at least one Z is

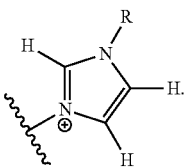

In certain embodiments, the present invention relates to the aforementioned salt, wherein Z is

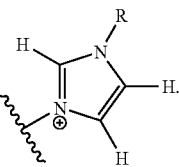

In certain embodiments, the present invention relates to the aforementioned salt, wherein at least one Z is

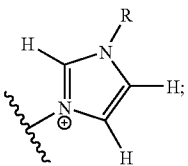

and R is alkyl.

In certain embodiments, the present invention relates to the aforementioned salt, wherein Z is

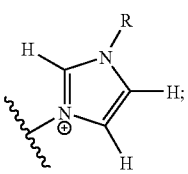

and R is alkyl.

In certain embodiments, the present invention relates to the aforementioned salt, wherein at least one Z is

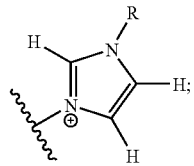

and R is —CH$_3$, —CH$_2$CH$_3$, —CH$_2$CH$_2$CH$_3$, —CH$_2$CH$_2$CH$_2$CH$_3$, or —CH$_2$CH$_2$CH$_2$CH$_2$CH$_3$.

In certain embodiments, the present invention relates to the aforementioned salt, wherein Z is and R is —CH$_3$, —CH$_2$CH$_3$, —CH$_2$CH$_2$CH$_3$, —CH$_2$CH$_2$CH$_2$CH$_3$, or —CH$_2$CH$_2$CH$_2$CH$_2$CH$_3$.

In certain embodiments, the present invention relates to the aforementioned salt, wherein W—[Z]$_3$ is [D]-W—[Z]$_2$; and D is selected from the group consisting of -AH, -AOH, —CH(OAH)(AOH), -(p-AH)Ph, and —Si(OH)(AH); A is, independently for each occurrence, —(CQ$_2$)$_p$-; Q is, independently for each occurrence, hydrogen or methyl; and r is, independently for each occurrence, 0-40 inclusive.

In certain embodiments, the present invention relates to the aforementioned salt, wherein W—[Z]$_3$ is [D]-W—[Z]$_2$; and D is selected from the group consisting of —CH$_2$CH$_3$, —CH$_2$CH$_2$OH, —CH(OCH$_2$CH$_3$)(CH$_2$OH), -(p-CH$_2$CH$_2$)Ph, and —Si(OH)(CH$_3$).

In certain embodiments, the present invention relates to the aforementioned salt, wherein said cationic component is W—[Z]$_4$.

In certain embodiments, the present invention relates to the aforementioned salt, wherein said anionic component is X—[Y]$_2$; X is -A-, -AO(AO)$_q$A-, -ANH(ANH)$_q$A-; A is, independently for each occurrence, —(CQ$_2$)$_p$-; Q is, independently for each occurrence, hydrogen or methyl; and p is, independently for each occurrence, 0-40 inclusive.

In certain embodiments, the present invention relates to the aforementioned salt, wherein A is absent, or selected, independently for each occurrence, from the group consisting of —CH$_2$—, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

In certain embodiments, the present invention relates to the aforementioned salt, wherein said anionic component is X—[Y]$_2$; X is —(CH$_2$)$_q$—, —CH$_2$—O—(CH$_2$O)$_q$CH$_2$—, —CH$_2$O(CH$_2$CH$_2$O)$_q$CH$_2$—, —CH$_2$CH$_2$—O—(CH$_2$CH$_2$CH$_2$O)$_q$CH$_2$CH$_2$—, —CH$_2$CH$_2$CH$_2$—O—(CH$_2$CH$_2$CH$_2$CH$_2$O)$_q$CH$_2$CH$_2$CH$_2$—, —CH$_2$NH(CH$_2$NH)$_q$CH$_2$—, —CH$_2$NH(CH$_2$CH$_2$NH)$_q$CH$_2$—, —CH$_2$CH$_2$NH(CH$_2$CH$_2$CH$_2$NH)$_q$CH$_2$CH$_2$—, or —CH$_2$CH$_2$CH$_2$NH(CH$_2$CH$_2$CH$_2$CH$_2$NH)$_q$CH$_2$CH$_2$CH$_2$—; and q is 0-40 inclusive.

In certain embodiments, the present invention relates to the aforementioned salt, wherein said anionic component is X—[Y]$_2$; X is —CH$_2$OCH$_2$CH$_2$OCH$_2$—, —(CH$_2$)$_{10}$—, or poly(acrylonitrile-co-butadiene).

In certain embodiments, the present invention relates to the aforementioned salt, wherein said anionic component is X—[Y]$_3$; X is C(R')(A-)$_3$, C(R')[(AO)$_p$A-]$_3$, C(R')[(ANH)$_p$A-]$_3$, N(A)$_3$, N[(AO)$_p$A-]$_3$, or N[(ANH)$_p$A-]$_3$; A is, independently for each occurrence, —(CQ$_2$)$_p$-; Q is, independently for each occurrence, hydrogen or methyl; p is, independently for each occurrence, 0-40 inclusive; and R' is hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano.

In certain embodiments, the present invention relates to the aforementioned salt, wherein said anionic component is X—[Y]$_3$; X is C(R')(A-)$_3$, C(R')[(AO)$_p$A-]$_3$, or C(R')[(ANH)$_p$ A-]$_3$; A is, independently for each occurrence, —(CQ$_2$)$_p$-; Q is, independently for each occurrence, hydrogen or methyl; p is, independently for each occurrence, 0-10 inclusive; and R' is hydrogen, halogen, azide, alkyl, aralkyl, alkenyl, alkynyl, cycloalkyl, hydroxyl, alkoxy, aryloxy, aryl, heteroaryl, heteroaralkyl, heteroaryloxy, amino, alkylamino, arylamino, heteroarylamino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, trifluoromethyl, and cyano.

In certain embodiments, the present invention relates to the aforementioned salt, wherein said anionic component is X—[Y]$_3$; X is N(A)$_3$, N[(AO)$_p$A-]$_3$, or N[(ANH)$_p$A-]$_3$; A is, independently for each occurrence, —(CQ$_2$)$_p$-; Q is, independently for each occurrence, hydrogen or methyl; and p is, independently for each occurrence, 0-10 inclusive.

In certain embodiments, the present invention relates to the aforementioned salt, wherein A is absent, or selected, independently for each occurrence, from the group consisting of —CH$_2$—, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

In certain embodiments, the present invention relates to the aforementioned salt, wherein said anionic component is X—[Y]$_4$; X is C(ACH$_2$—)$_4$, C[(AO)$_p$A-]$_4$, C[(ANH)$_p$A-]$_4$, (-A)$_2$N(AO)$_p$AN(A-)$_2$, or (-A)$_2$N(ANH)$_p$AN(A-)$_2$; A is, independently for each occurrence, —(CQ$_2$)$_p$-; Q is, independently for each occurrence, hydrogen or methyl; and p is, independently for each occurrence, 0-40 inclusive.

In certain embodiments, the present invention relates to the aforementioned salt, wherein A is absent, or selected, independently for each occurrence, from the group consisting of —CH$_2$—, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

In certain embodiments, the present invention relates to the aforementioned salt, wherein W is C(ACH$_2$—)$_4$, C[(AO)$_p$A-]$_4$, C[(ANH)$_p$A-]$_4$, (-A)$_2$N(AO)$_p$AN(A-)$_2$, or (-A)$_2$N(ANH)$_p$AN(A-)$_2$; A is, independently for each occurrence, —(CQ$_2$)$_p$-; Q is, independently for each occurrence, hydrogen or methyl; and p is, independently for each occurrence, 0-40 inclusive.

In certain embodiments, the present invention relates to the aforementioned salt, wherein W—[Z]$_4$ is [Z]$_3$—W—[N(R")$_3$] or [Z]$_3$—W—[P(R")$_3$]; R" is, independently for each occurrence, hydrogen, alkyl, aryl, or aralkyl.

In certain embodiments, the present invention relates to the aforementioned salt, wherein W—[Z]$_4$ is [Z]$_2$—W—[N(R")$_3$]$_2$ or [Z]$_2$—W—[P(R")$_3$]$_2$; and R" is hydrogen, alkyl, aryl, or aralkyl.

In certain embodiments, the present invention relates to the aforementioned salt, wherein W—[Z]$_4$ is [Z]-W—[N(R")$_3$]$_3$ or [Z]-W—[P(R")$_3$]$_3$; and R" is hydrogen, alkyl, aryl, or aralkyl.

In certain embodiments, the present invention relates to the aforementioned salt, wherein W—[Z]$_4$ is W—[N(R")$_3$]$_4$ or W—[P(R")$_3$]$_4$; and R" is hydrogen, alkyl, aryl, or aralkyl.

In certain embodiments, the present invention relates to the aforementioned salt, wherein W—[Z]$_4$ is W—[NH$_3$]$_4$.

In certain embodiments, the present invention relates to the aforementioned salt, wherein W—[Z]$_4$ is W—[P(CH$_2$CH$_2$CH$_2$CH$_2$CH$_2$CH$_3$)$_3$]$_4$.

In certain embodiments, the present invention relates to the aforementioned salt, wherein at least one Z is

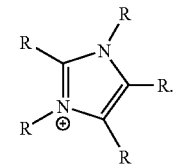

In certain embodiments, the present invention relates to the aforementioned salt, wherein Z is

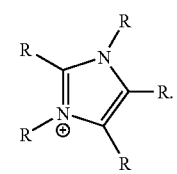

In certain embodiments, the present invention relates to the aforementioned salt, wherein at least one Z is

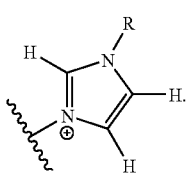

In certain embodiments, the present invention relates to the aforementioned salt, wherein Z is

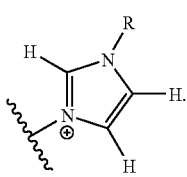

In certain embodiments, the present invention relates to the aforementioned salt, wherein at least one Z is

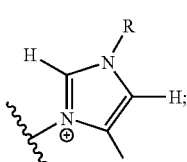

and R is alkyl.

In certain embodiments, the present invention relates to the aforementioned salt, wherein Z is

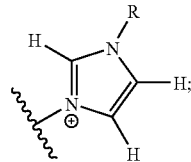

and R is alkyl.

In certain embodiments, the present invention relates to the aforementioned salt, wherein at least one Z is

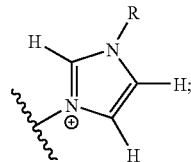

and R is —$CH_3$, —$CH_2CH_3$, —$CH_2CH_2CH_3$, —$CH_2CH_2CH_2CH_3$, or —$CH_2CH_2CH_2CH_2CH_3$.

In certain embodiments, the present invention relates to the aforementioned salt, wherein Z is

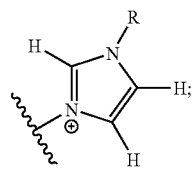

and R is —$CH_3$, —$CH_2CH_3$, —$CH_2CH_2CH_3$, —$CH_2CH_2CH_2CH_3$, or —$CH_2CH_2CH_2CH_2CH_3$.

In certain embodiments, the present invention relates to the aforementioned salt, wherein W—$[Z]_4$ is $[D]$-W—$[Z]_3$; and D is selected from the group consisting of -AH, -AOH, —CH(OAH)(AOH), -(p-AH)Ph, and —Si(OH)(AH); A is, independently for each occurrence, —$(CQ_2)_p$-; Q is, independently for each occurrence, hydrogen or methyl; and r is, independently for each occurrence, 0-40 inclusive.

In certain embodiments, the present invention relates to the aforementioned salt, wherein W—$[Z]_4$ is $[D]$-W—$[Z]_3$; and D is selected from the group consisting of —$CH_2CH_3$, —$CH_2CH_2OH$, —$CH(OCH_2CH_3)(CH_2OH)$, -(p-$CH_2CH_2$)Ph, and —Si(OH)($CH_3$).

Another aspect of the invention relates to a salt comprising an anionic component and a cationic component, wherein:

said anionic component is selected from the group consisting of polyacrylic acid, $[O_2CCH_2OCH_2CH_2OCH_2CO_2]^{-2}$, $[O_2CC_{10}H_{20}OCO_2]^{-2}$, [dicarboxy terminated poly(acrylonitrile-co-butadiene)]$^{-2}$, and $[(O_2CCH_2)_2NCH_2CH_2N(CH_2CO_2)_2]^{-4}$; and said cationic component is selected from the group consisting of $[^{Me}$Imid-$CH_2CH_2OCH_2CH_2OCH_2CH_2$-Imid$^{Me}]^{+2}$, [TIME$^{Me}]^{+3}$, $[H_3NCH_2CH_2OCH_2CH_2OCH_2CH_2NH_3]^{+2}$, $[(NH_3CH_2CH_2)_3NH]^{+4}$, $[HC(O[CH_2CH(CH_3)O]_yCH_2CH(CH_3)NH_3)$—$(CH_2O[CH_2CH(CH_3)O]_xCH_2CH(CH_3)NH_3)$—$(CH_2O[CH_2CH(CH_3)O]_zCH_2CH(CH_3)NH_3)]^{+3}$, $[(CH_3CH_2CH_2CH_2)_3P$—$C_{10}H_{20}$—$P(CH_2CH_2CH_3)_3]^{+2}$; wherein x is 0-81 inclusive; y is 0-81 inclusive; z is 0-81 inclusive; and the sum of x, y and z is equal to 81.

In certain embodiments, the present invention relates to the aforementioned salt, wherein said anionic component is $[O_2CCH_2OCH_2CH_2OCH_2CO_2]^{-2}$.

In certain embodiments, the present invention relates to the aforementioned salt, wherein said anionic component is $[O_2CC_{10}H_{20}CO_2]^{-2}$.

In certain embodiments, the present invention relates to the aforementioned salt, wherein said anionic component is [dicarboxy terminated poly(acrylonitrile-co-butadiene)]$^{-2}$.

In certain embodiments, the present invention relates to the aforementioned salt, wherein said anionic component is $[(O_2CCH_2)_2NCH_2CH_2N(CH_2CO_2)_2]^{-4}$.

In certain embodiments, the present invention relates to the aforementioned salt, wherein said anionic component is $[(O_2CCH_2)_2NCH_2CH_2N(CH_2CO_2)_2]^{-4}$.

In certain embodiments, the present invention relates to the aforementioned salt, wherein said anionic component is polyacrylic acid.

In certain embodiments, the present invention relates to the aforementioned salt, wherein said cationic component is $[^{Me}$Imid-$CH_2CH_2OCH_2CH_2CH_2CH_2OCH_2CH_2$-Imid$^{Me}]^{+2}$.

In certain embodiments, the present invention relates to the aforementioned salt, wherein said cationic component is [TIME$^{Me}]^{+3}$.

In certain embodiments, the present invention relates to the aforementioned salt, wherein said cationic component is $[H_3NCH_2CH_2OCH_2CH_2OCH_2CH_2NH_3]^{+2}$.

In certain embodiments, the present invention relates to the aforementioned salt, wherein said cationic component is $[(NH_3CH_2CH_2)_3NH]^{+4}$.

In certain embodiments, the present invention relates to the aforementioned salt, wherein said cationic component is selected from the group consisting of $[HC(O[CH_2CH(CH_3)O]_yCH_2CH(CH_3)NH_3)$—$(CH_2O[CH_2CH(CH_3)O]_xCH_2CH(CH_3)NH_3)$—$(CH_2O[CH_2CH(CH_3)O]_zCH_2CH(CH_3)NH_3)]^{+3}$; wherein x is 0-81 inclusive; y is 0-81 inclusive; z is 0-81 inclusive; and the sum of x, y and z is equal to 81.

In certain embodiments, the present invention relates to the aforementioned salt, wherein said cationic component is $[(CH_3(CH_2)_5)_3P$—$C_{10}H_{20}$—$P$—$((CH_2)_5CH_3)_3]^{+2}$.

Selected Synthetic Approaches to the Cationic and Anionic Components of the Invention. Two approaches, of the many possible approaches, for the formation of the compounds of the invention are shown in FIG. 4. One approach to the synthesis of the di(cationic) and di(anionic) components of the instant invention would be to synthesis two cationic (or anionic) components which could then be reacted together to form the desired di(cation) or the di(anion). The coupling could be achieved via a number of different reactions, including, for example, alkylation, cycloadditon, amination, and arylation. In principle any carbon-carbon bond forming reaction could be used to couple the individual cations or anions.

Another approach to the synthesis of the inventive compounds would be to react a cation- or anion-containing compound with a polymer which contains reactive side chains. By this method, a poly(cation) or poly(anion) could be easily assembled. As will be evident to one skilled in the art, they are many additional ways the compounds of the invention may be synthesized.

Various Applications of Ionic Liquids. The ionic liquids according to the present invention may be used for a wide range of purposes; for example, the liquids are useful for carrying out applications, such as chemical reactions in preparative chemistry where a polar but non-aqueous solvent or a solvent with negligible vapor pressure is required.

The ionic liquids according to the present invention may also be employed as lubricant fluids. They can have lubricant properties for a wide range of temperature (for example, from −50° C. to 350° C.) with no vapor pressure and may be used for a wide range of purposes, for example, as self-healing boundary lubricants suitable for microelectromechanical systems (MEMS). MEMS devices are widely utilized, for example, in miniature satellites, airflow control, sensors, actuators, accelerometers, gyroscopes, microwave switches, aircraft turbine engines, and unmanned aerial vehicles.

The ionic liquids according to the present invention may, when the inventive material melts above room temperature, be melted and cooled to make film. In addition, when the ionic material dissolves in a solution, the solvent can be evaporated, thereby coating a surface with the ionic liquid. Further, the ionic liquids according to the present invention may be extruded to make fibers, or used for injection modeling.

The ionic liquids according to the present invention may also be employed as thermal storage fluids. They may further be employed as inert media, for example, for dissolving ionic species, such as transition metal complexes, and, either alone, or after complexing with other metal ions, as catalysts, or as chemical reagents.

Solvent system applications wherein a polar but non-aqueous solvent is required for which the ionic liquids of the present invention are useful include cellulose recycling, catalytic cracking reactions such as polyethylene recycling, chiral catalysis, coupling reactions, such as the Heck reaction, sulfonation reactions, nitration reactions, oxidation reactions, nucleophilic substitution reactions, olefin polymerization reactions, actinide extractions, alkylation reactions, hydroformylation reactions, dimerization reactions, hydrogenation reactions, Diels-Alder reactions, metathesis reactions, arylation reactions, Friedel-Crafts reactions, and the like.

The ionic liquids of the present invention may be used as non-aqueous electrolytes in electrochemical devices such as electrochemical capacitors, photovoltaic devices, potentiometric and voltametric electrochemical sensors, batteries, fuel cells and electrodeposition devices. The present invention therefore includes such electrochemical devices in which a positive electrode and a negative electrode are in conductive contact with a non-aqueous electrolyte essentially consisting of an ionic liquid of the present invention. Other conventional electrolyte additives may be present. The devices are otherwise conventional and require no further description. One having ordinary skill in the art will understand how to use ionic liquids according to the present invention as a non-aqueous electrolyte for such devices.

The ionic liquids of the invention that preferentially dissolve certain gaseous species can be used in conventional gas absorption applications. The non-volatile nature of ionic liquids plays two important roles. First, there will be no cross-contamination of the gas stream by the solvent during operation. This means no solvent loss and no air pollution. Second, regeneration of the solvent is easy; a simple flash or mild distillation step is all that is required to remove the gas from the solvent, again with no cross-contamination.

In addition to their use as conventional absorbents, ionic liquids may be immobilized on a support and used in a supported liquid membrane (SLM). The membrane will work if a gas preferentially dissolves in the liquid. SLMs may be used in a continuous separation process without a regeneration step. Conventional SLM technology is undermined by the fact that the liquid in which the gas dissolves eventually evaporates, thus rendering the membrane useless. Since ionic liquids are completely non-volatile, this problem is eliminated.

Ionic liquids also find use in the conversion of brown coal and oil shale into value-added products, such as alternative synthetic fuels and/or high-quality chemical feedstocks. For example, 1-butyl-3-methyl imidazolium, has been used to extract organic compounds from Estonian oil shale kerogen at various temperatures. Results at 175° C. yielded soluble products with an increase of ten times over that obtained using conventional organic solvents.

Bronsted-acidic ILs also act as proton shuttles, functionally carrying protons from acidic resin surfaces (e.g., Nafion) to the surrounding medium, where they are more free to react than if the proton is held at the polymer surface. Moreover, the Bronsted-acidic ILs have essentially no vapor pressure when dissolved in water. For example, a relatively concentrated solution of HCl gives off HCl gas; in contrast, a Bronsted-acidic IL gives off no detectable gaseous acid.

Many product streams, particularly in the field of petroleum chemistry, include olefins and non-olefins. For example, ethane crackers tend to produce a mixture of ethane and ethylene. The ethylene is typically separated from the ethane via distillation. Because the boiling points of ethylene and ethane are relatively close to one another, the distillation is typically done at very low temperatures and/or high pressures; the separation is relatively expensive. The same problems are observed when separating propane from propylene in dehydrogenation facilities. Ionic liquids are useful in separating such mixtures. For example, an ionic liquid with a pendant functional group that coordinates the pi-bond of an olefin may be used to dissolve selectively the olefinic components of such a mixture. Likewise, an ionic liquid with a pendant functional group that coordinates a transition metal capable of coordinating the pi-bond of an olefin may be used to dissolve selectively the olefinic components of such a mixture. In either case, the dissolved olefins subsequently can be isolated by desorption.

Below are some representative examples of ionic liquids and their uses as reported in the literature; the inventive ionic liquids may likewise be used. As mentioned in-part above, ionic liquids have been used as solvents in catalytic reactions, such as the use of alkyl containing hydrohalide salts which can be used as solvent for alkylation, arylation, and polymerization, as well as an electrolyte for batteries (U.S. Pat. No. 5,731,101); ionic liquids have been used for catalysis (U.S. Pat. No. 6,703,507); ionic liquids have been used for hydroformylation of olefinic compounds (U.S. Pat. No. 5,874,638); ionic liquids have been formed from diaryl-anellated bicyclo [2.2.n] compounds (U.S. Pat. No. 6,977,312); ionic liquids have been used on solid support for homogeneous hydroformylation (*J. Am. Chem. Soc.* 2002, 124(44), 12932-12933); as well as being used to stabilize rhodium nanoparticles for benzene hydrogenation (*J. Am. Chem. Soc.* 2005, 127(27), 9694-9695).

In addition, ionic liquids are well known as solvents for a variety of applications such as extracting organosulfur compounds from hydrocarbons (U.S. Pat. No. 7,001,504); as general solvents (U.S. Pat. No. 6,379,634); to dissolve cellose (*J. Am. Chem. Soc.* 2002, 124(18), 4974-4975); to dissolve and regenerate *Bombyx mori* Silk Fibroin (*J. Am. Chem. Soc.* 2004, 126(44), 14350-14351); as a suitable phase for multi-step parallel synthesis of arrays of isoxazolines (*Org. Lett.* 2003, 5(22), 4029-4031); for the preparation of silyl enol ethers using (bistrimethylsilyl)acetamide (*Org. Lett.* 2001, 3(7), 1037-1039); as catalysts and reaction medium for the Michael addition of active methylene compounds to conjugated ketones, carboxylic esters, and nitrites (*Org. Lett.* 2005, 7(14), 3049-3052); for the photoreduction of benzophenones by amines at room-temperature (*Org. Lett.* 2002, 4(6), 917-919).

Further, ionic liquids have also found utility in fuel cells technologies (U.S. Pat. No. 6,977,122) and well as electronic devices such as capacitors (U.S. Pat. No. 6,965,509) with poly (3,4-alkylenedioxythiophene) or electric double-layer capacitors (U.S. Pat. No. 6,914,768). Ionic liquids are also being explored as liquid crystalline materials (*Macromolecules* 1995, 28, 8877-8880). Ionic liquids have also been used in solar cells, to increase efficiency (*Chem. Mater.* 2004, 16(14), 2694-2696).

Ionic liquids have also been used as stationary phases in gas chromatography (*Anal. Chem.* 2004, 76(22), 6819-6822). As already mentioned herein, ionic liquids can also be used for separation and solubilization of gases (*Ind. Eng. Chem. Res.;* 2004; 43(5); 1296-1301).

In certain embodiments, ionic liquids of the present invention are surfactants. Surfactants are soluble chemical compounds that when added to a mixture of two liquids reduce the surface tension between said liquids. Surfactant aggregation has been observed in room temperature ionic liquids (*Chem. Comm,* 2003, 2444-2445).

Interestingly, the formation of nanoclusters in ionic liquids have also been reported (*J. Am. Chem. Soc.;* 2005; 127(16); 5758-5759). Ionic liquids have also been used to prepared Rare-Earth Iodides such $[SEt_3]_3[LnI_6]$, where Ln is Nd or Sm (*Inorg. Chem.* 2005, 44(23), 8168-8169); as well as $PbCrO_4$ and $Pb_2CrO_5$ rods, via a microwave-assisted ionic liquid method (*Cryst. Growth Des.* 2005, 5(2), 505-507).

Ionic liquids can also be used as solvent for enzymatic reactions such as the lipase-catalyzed glucose fatty acid ester synthesis (*Org. Lett.;* 2005; 7(14); 3097-3098). Moreover, ionic liquids are considered green solvents (see, for example, "Ionic Liquids as Green Solvents Progress and Prospects" Edited by Robin D. Rogers (The University of Alabama) and Kenneth R. Seddon (The Queen's University of Belfast). American Chemical Society: Washington, D.C. (Distributed by Oxford University Press). 2003. ISBN 0-8412-3856-1). Ionic liquids have been reported for use as an industrial cleanup solution (*Environ. Sci. Technol. A-Pages* 2001, 35(19), 410 A-413). Sonochemistry and sonoluminescence of room-temperature ionic liquids have also been reported (*J. Am. Chem. Soc.* 2003, 125(37), 11138-11139).

Selected Methods of the Invention. One aspect of the present invention is a method of preparing an ionic liquid in solution, comprising the step adding a solute to any one of the aforementioned salts. Alternatively, the ionic liquid or vicoelastic can be prepared in one step by mixing the two neat solids and warming the mixture.

Another aspect of the present invention is a method of catalyzing chemical reaction, comprising the step of exposing a reactant mixture to any one of the aforementioned salts.

In certain embodiments, the present invention relates to the aforementioned method and the attendant definitions, wherein said chemical reaction is acid-catalyzed or base-catalyzed.

Another aspect of the present invention is the use of any one of the aforementioned salts, and a polar organic liquid, as an electrolyte in a electrochemical cell.

Another aspect of the present invention is the use of the any one of the aforementioned salts, and a polar organic liquid, as an electrolyte in a capacitor.

In certain embodiments, said polar organic liquid is selected from the group consisting of linear ethers, cyclic ethers, esters, carbonates, lactones, nitriles, amides, sulfones and sulfolanes.

In certain embodiments, said polar organic liquid is selected from the group consisting of diethylether, dimethoxyethane, tetrahydrofuran, dioxane, dioxolane, methyltetrahydrofuran, methyl formate, ethyl formate, methyl propionate, propylene carbonate, ethylene carbonate, dimethyl carbonate, diethyl carbonate, ethylmethyl carbonate, dibutyl carbonate, butyrolactones, acetonitrile, benzonitrile, nitromethane, nitrobenzene, dimethylformamide, N-methylpyrrolidone, dimethylsulfone, tetramethylene sulfone, sulfolane and thiophene.

One aspect of the present invention is using any one of the aforementioned salts as a surfactant. In one embodiment the present invention relates to a method of preventing or decreasing an emulsion in a sample comprising the step of adding said salt to said sample.

Another aspect of the present invention is the method of coating an object comprising the step of exposing said object to a solution consisting of any one of the aforementioned salts and a solvent; removing said solvent.

Another aspect of the present invention is the use of the inventive salts to make gels. Gels are three-dimensional polymeric materials which exhibit the ability to swell in water and to retain a fraction of water within the structure without dissolving. The physical properties exhibited by gels such as water content, sensitivity to environmental conditions (e.g., pH, temperature, solvent, stress), soft, adhesivity, and rubbery consistency are favorable for biomedical and biotechnological applications. Indeed, gels may be used as coatings (e.g. biosensors, catheters, and sutures), as "homogeneous" materials (e.g. contact lenses, burn dressings, and dentures), and as devices (e.g. artificial organs and drug delivery systems) (U.S. Patent 2004/0086479; hereby incorporated by reference in its entirety). Yet another aspect of the invention relates to the use of the inventive salts to make plastics that are elastic materials. Such plastics may be prepared by any of the standard methods, e.g., injection molding or casting from solution. An injection molding process may be practiced at ambient temperature or an elevated temperature. The inventive salts may be cast into plastics from a polar solvent, a non-polar solvent or a mixture of solvents.

Definitions. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "ionic liquid" or "IL" as used herein means an salt or hydrate thereof with a melting point less than about 150° C. In a preferred embodiment, the ionic liquid has a melting point of less than about 100° C. In a preferred embodiment, the ionic liquid has a melting point of less than about 50° C. In a preferred embodiment, the ionic liquid has a melting point of less than about room temperature. The ionic liquids of the present invention may comprise one or more compounds. Thus, the ionic liquid may be a pure compound or may be a mixture of compounds. Each compound comprises an anion or a mixture of anions; and a cation or a mixture of cations.

As used herein, a "viscoelastic" material is a liquid (or solid) with both viscous and elastic properties. A viscoelastic liquid will deform and flow under the influence of an applied shear stress, but when the stress is removed the liquid will slowly recover from some of the deformation.

As used herein, "X—[Y]$_m$," indicates an "X" group (e.g. a small molecule or a polymer) with "m" pendant "Y" groups (e.g. anionic or cationic moieties), wherein m is an integer. Below are representative examples for when m is 2, 3 or 4.

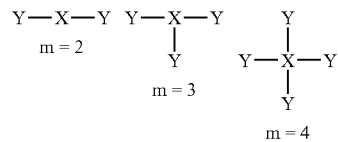

A chemical example of a m=2 compound is $HO_2CCH_2O[CH_2CH_2O]_2CH_2CO_2H$. A chemical example of a m=3 compound is $C(CH_3)(CH_2CO_2H)_3$. A chemical example of a m=4 compound is $C(CH_2CH_2CO_2H)_4$. In addition, as described herein, "X" can be a molecule which can have several pendant "Y" groups; a representative example of when m=9 is given below.

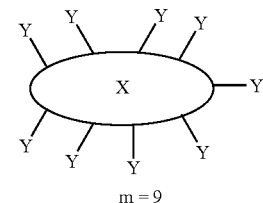

As used herein, "TEG" is an abbreviation for tritheylene glycol. TEG has the molecular formula of $HOCH_2CH_2OCH_2CH_2OCH_2CH_2OH$. In certain embodiments TEG is used as a tether to connect two anionic or cationic moieties. For example, "$NaO_2C$-TEG-$CO_2Na$" is an abbreviation for $NaO_2C-CH_2OCH_2CH_2OCH_2-CO_2Na$. As used herein, "TetraEG" is an abbreviation for tetraethylene glycol. TetraEG has the molecular formula of $HOCH_2CH_2OCH_2CH_2OCH_2CH_2OCH_2CH_2OH$. In certain embodiments TetraEG is used as a tether to connect two anionic or cationic moieties. Other polyetheylene glycols (e.g. pentaethyleneglycols, hexaethyleneglycols, or other larger ethylene glycols) may be used in the invention. In addition, the ethylene units may be replaced by other alkyl spacers (e.g. propylene or methylene) or aryl spacers, and the spacers may vary in a given tether (e.g. —$CH_2CH_2OCH_2CH_2CH_2OCH_2OCH_2CH_2OCH_2$—). Branched polyether chains may also be used in the invention.

As used herein, "Cl$^{Me}$Imid-" is an abbreviation for a

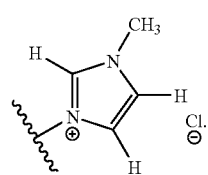

Other such structures, such as Br$^{Et}$Imid- and Cl$^{i-Pr}$Imid-, may also be used in the invention As used herein, "TIME$^{Me}$Cl" is an abbreviation for

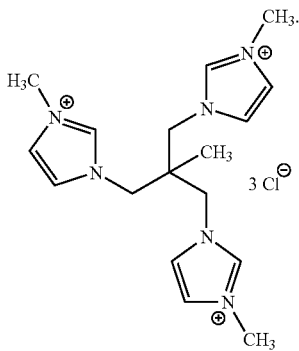

Other such structures, such as TIME$^{Et}$Br and TIME$^{Pr}$Cl, may also be used in the invention. In addition, in certain embodiments, the methyl group on the central carbon can be replaced with other alkyl groups.

As used herein, "EDTA" is an abbreviation for ethylenediaminetetraacetic acid. EDTA has the molecular formula of $(HO_2CCH_2)_2NCH_2CH_2N(CH_2CO_2H)_2$. Other such branched polyamines may be used in the invention, for example JEFFAMINE® T-5000 described below.

As used herein, "JEFFAMINE® T-5000" is primary polyether triamine of approximately 5000 molecular weight. It is a clear, almost colorless, viscous, liquid product. It has the following structure where the sum of x, y, and z is about 81.

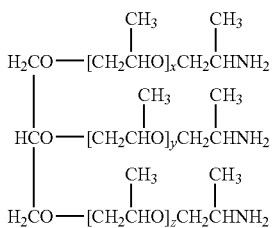

As used herein, "TETA" is an abbreviation for triethylenetetramine. TETA has the molecular formula of $H_2NCH_2CH_2NHCH_2CH_2NHCH_2CH_2NH_2$.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 80 or fewer carbon atoms in its backbone (e.g., $C_1$-$C_{80}$ for straight chain, $C_3$-$C_{80}$ for branched chain), and alternatively, about 30 or fewer. Likewise, cycloalkyls have from about 3 to about 10 carbon atoms in their ring structure, and alternatively about 5, 6 or 7 carbons in the ring structure. As used herein, "fluoroalkyl" denotes an alkyl where one or more hydrogens have been replaced with fluorines.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, phosphonium, carbonyl, carboxyl, silyl, alkylthio, sulfonyl, sulfonamido, ketone, aldehyde, ester, heterocyclyl, aromatic or heteroaromatic moieties, trifluoromethyl, cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, phosphonium, carbonyl, carboxyl, silyl, alkylthio, sulfonyl, ketone, aldehyde, ester, a heterocyclyl, an aromatic or heteroaromatic moiety, trifluoromethyl, cyano, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, phosphonium, carbonyl, carboxyl, silyl, alkylthio, sulfonyl, ketone, aldehyde, ester, a heterocyclyl, an aromatic or heteroaromatic moiety, trifluoromethyl, cyano, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on page 560 of "Advanced Inorganic Chemistry" by Cotton and Wilkinson, that is, for example, monovalent anionic groups sufficiently electronegative to exhibit a positive Hammett sigma value at least equaling that of a halide (e.g., CN, OCN, SCN, SeCN, TeCN, N$_3$, and C(CN)$_3$).

The terms "amine" and "amino" are art-recognized and refer to both unsubstituted and substituted amines, e.g., a moiety that may be represented by the general formulas:

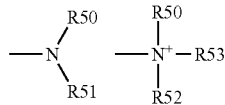

wherein R50, R51, R52 and R53 each independently represent a hydrogen, an alkyl, an alkenyl, —(CH$_2$)$_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

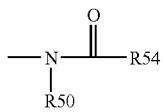

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

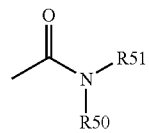

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

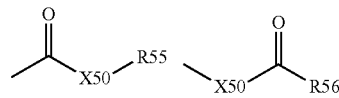

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

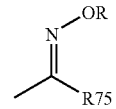

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

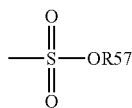

in which R57 is an electron pair, hydrogen, alkyl, cycloalkyl, or aryl.

The term "sulfate" is art recognized and includes a moiety that may be represented by the general formula:

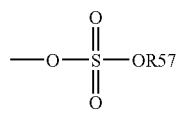

in which R57 is as defined above.

The term "sulfonamido" is art recognized and includes a moiety that may be represented by the general formula:

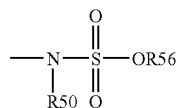

in which R50 and R56 are as defined above.

The term "sulfamoyl" is art-recognized and refers to a moiety that may be represented by the general formula:

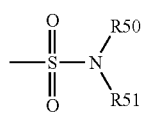

in which R50 and R51 are as defined above.

The term "sulfonyl" is art-recognized and refers to a moiety that may be represented by the general formula:

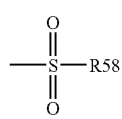

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The term "phosphoryl" is art-recognized and may in general be represented by the formula:

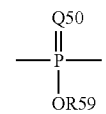

wherein Q50 represents S or O, and R59 represents hydrogen, a lower alkyl or an aryl. When used to substitute, e.g., an alkyl, the phosphoryl group of the phosphorylalkyl may be represented by the general formulas:

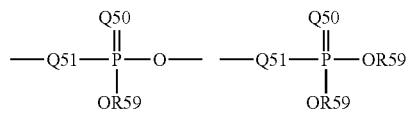

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

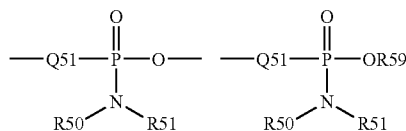

wherein Q51, R50, R51 and R59 are as defined above.

The term "phosphonamidite" is art-recognized and may be represented in the general formulas:

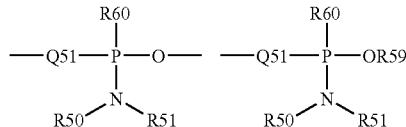

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

While several embodiments of the present invention are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

EXEMPLIFICATION

The invention now being generally described, it will be more readily understood by reference to the following examples which are included merely for purposes of illustration of certain aspects and embodiments of the present invention, and are not intended to limit the invention.

Example 1

$NaO_2C$-TetraEG-$CO_2Na$ with $Cl^{Me}$Imid-TetraEG-Imid$^{Me}$Cl. $NaO_2C$-TetraEG-$CO_2Na$ (1 g, 3.76 mmol) and $Cl^{Me}$Imid-TetraEG-Imid$^{Me}$Cl (1.48 g, 3.76 mmol) were dissolved in de-ionized water (5 mL) then a solution of $AgNO_3$ (1.28, 7.52 mmol) in de-ionized water (2 mL) was added drop by drop under vigorous agitation. The precipitate compound (AgCl) was isolated by filtration under nitrogen and the filtrate was concentrated and dried under vacuum at 170° C. for 3 h to lead to a clear colorless viscous oil.

Example 2

$HO_2C$-TetraEG-$CO_2H$ with $Cl^{Me}$Imid-TetraEG-Imid$^{Me}$Cl. $HO_2C$-TetraEG-$CO_2H$ (1 g, 4.5 mmol) and $Cl^{Me}$Imid-TetraEG-Imid$^{Me}$Cl (1.77 g, 4.5 mmol) were dissolved in de-ionized water (5 mL) then a solution of $AgNO_3$ (1.53, 9.0 mmol) in de-ionized water (2 mL) was added drop by drop under vigorous agitation. The precipitate compound (AgCl) was isolated by filtration under nitrogen and the filtrate was concentrated and dried under vacuum at 170° C. for 3 h to lead to a clear colorless viscous oil.

Example 3

$HO_2C$-TetraEG-$CO_2H$ with TIME$^{Me}$Cl. $HO_2C$-TetraEG-$CO_2H$ (1 g, 4.5 mmol) and TIME$^{Me}$Cl (1.23 g, 3.00 mmol) were dissolved in de-ionized water (5 mL) then a solution of AgNO$_3$ (1.53 g, 9.0 mmol) in de-ionized water (2 mL) was added drop by drop under vigorous agitation. The precipitate compound (AgCl) was isolated by filtration under nitrogen and the filtrate was concentrated and dried under vacuum at 170° C. for 3 h to lead to a clear colorless viscous oil.

Example 4

EDTA with H$_2$N-TetraEG-NH$_2$. EDTA (1 g, 3.4 mmol) and H$_2$N-TetraEG-NH$_2$ (1.31 g, 6.8 mmol) were mixed in de-ionized water (5 mL) and heated to 80° C. under vigorous agitation for 30 min. The mixture was vacuum dried at 80° C. to lead to a clear colorless viscous oil.

Example 5

HO$_2$C-TetraEG-CO$_2$H with tris(2-aminoethyl)amine. HO$_2$C-TetraEG-CO$_2$H (1 g, 4.5 mmol) and tris(2-aminoethyl)amine (438 mg, 3.00 mmol) were mixed together at 80° C. under vacuum for 2 h to lead to a clear colorless viscoelastic oil.

Example 6

HO$_2$C-TetraEG-CO$_2$H with JAFFAMINE T-5000. HO$_2$C-TEG-CO$_2$H (1 g, 4.5 mmol) and JAFFAMINE T-5000 (15 g, 3.00 mmol) were mixed together at 80° C. under vacuum for 2 h to lead to a clear colorless viscous oil.

Example 7

HO$_2$C-TetraEG-CO$_2$H with TETA. HO$_2$C-TetraEG-CO$_2$H (1 g, 4.5 mmol) and TETA (320 mg, 2.25 mmol) were mixed together at 80° C. under vacuum for 2 h to lead to a clear colorless viscoelastic oil.

Example 8

Poly(acrylonitrile-co-butadiene), dicarboxy terminated with JAFFAMINE T-5000. Poly(acrylonitrile-co-butadiene), dicarboxy terminated (1 g, 0.26 mmol) and TETA (877 mg, 0.17 mmol) were mixed together at 80° C. under vacuum for 2 h to lead to a clear colorless viscous oil.

Example 9

EDTA with JAFFAMINE T-5000. EDTA (1 g, 3.4 mmol) and JAFFAMINE T-5000 (22.8 mg, 4.5 mmol) were mixed together at 80° C. under vacuum for 2 h. The EDTA is not soluble to it.

Example 10

HO$_2$C—C$_{10}$H$_2$O—CO$_2$H with TETA. HO$_2$C—C$_{10}$H$_2$O—CO$_2$H (1 g, 4.3 mmol) and TETA (317 mg, 2.17 mmol) were mixed together at 140° C. under vacuum for 2 h to lead to a solid.

Example 11

AgO$_2$C-TetraEG-CO$_2$Ag with TIME$^{Me}$Cl. TIME$^{Me}$Cl (700 mg, 1.66 mmol) was dissolved in de-ionized water (10 ml) and warmed to 80° C. AgO$_2$C-TetraEG-CO$_2$Ag (1 g, 2.48 mmol) was dissolved in warmed (80° C.) de-ionized water (20 ml) and added drop by drop under vigorous agitation to the previous solution. The mixture was allowed to react for 3 h at room temperature to get the fully precipitation of the silver chloride. After filtration of the silver chloride, the mixture was dried under vacuum at 170° C. for 3 h to lead to a clear colorless viscoelastic oil.

Example 12

HO$_2$C-TetraEG-CO$_2$H with H$_2$N-TetraEG-NH$_2$. HO$_2$C-TetraEG-CO$_2$H (1 g, 4.5 mmol) and H$_2$N-TetraEG-NH$_2$ (864 mg, 4.5 mmol) were mixed together (exothermic) to lead to a clear colorless viscous oil.

Example 13

(CH$_3$CH$_2$CH$_2$CH$_2$CH$_2$CH$_2$)$_3$P$^+$—C$_{10}$H$_{20}$—P$^+$(CH$_2$CH$_2$CH$_2$CH$_2$CH$_3$)$_3$,2Cl$^-$ with HO$_2$C—C$_{10}$H$_{20}$—CO$_2$H. (CH$_3$CH$_2$CH$_2$CH$_2$CH$_2$CH$_2$)$_3$P$^+$—C$_{10}$H$_{20}$—P$^+$(CH$_3$CH$_2$CH$_2$CH$_2$CH$_2$)$_3$,2Cl$^-$ (1 g, 1.6 mmol) and HO$_2$C—C$_{10}$H$_{20}$—CO$_2$H (373 mg, 1.6 mmol) were mixed together at 80° C. under vacuum for 2 h to lead to a clear colorless viscous oil.

Example 14

(CH$_3$CH$_2$CH$_2$CH$_2$CH$_2$CH$_2$)$_3$P$^+$—C$_{10}$H$_{20}$—P$^+$(CH$_2$CH$_2$CH$_2$CH$_2$CH$_3$)$_3$,2Cl$^-$ with EDTA. (CH$_3$CH$_2$CH$_2$CH$_2$CH$_2$CH$_2$)$_3$P$^+$—C$_{10}$H$_{20}$—P$^+$(CH$_2$CH$_2$CH$_2$CH$_2$CH$_3$)$_3$,2Cl$^-$ (1 g, 1.6 mmol) and EDTA (237 mg, 0.8 mmol) were mixed together at 80° C. under vacuum for 2 h to lead to a clear colorless viscous oil.

Example 15

(CH$_3$CH$_2$CH$_2$CH$_2$CH$_2$CH$_2$)$_3$P$^+$—C$_{10}$H$_{20}$—P$^+$(CH$_2$CH$_2$CH$_2$CH$_2$CH$_3$)$_3$,2Cl$^-$ with polyacrylic acid (240,000 Mw at 25% in water). (CH$_3$CH$_2$CH$_2$CH$_2$CH$_2$CH$_2$)$_3$P$^+$—C$_{10}$H$_{20}$—P$^+$(CH$_2$CH$_2$CH$_2$CH$_2$CH$_2$CH$_3$)$_3$,2Cl$^-$ (1 g, 1.3 mmol) and Polyacrylic Acid (734 mg, 0.76 µmol) were mixed together at 100° C. under vacuum for 2 h to remove water and lead to a clear colorless viscoelastic.

Example 16

(CH$_3$CH$_2$CH$_2$CH$_2$CH$_2$CH$_2$)$_3$P$^+$—C$_{10}$H$_{20}$—P$^+$(CH$_2$CH$_2$CH$_2$CH$_3$)$_3$,2Cl$^-$ with HO$_2$C—C$_8$F$_{16}$—CO$_2$H. (CH$_3$CH$_2$CH$_2$CH$_2$CH$_2$CH$_2$)$_3$P$^+$—C$_{10}$H$_{20}$—P$^+$(CH$_2$CH$_2$CH$_2$CH$_2$CH$_3$)$_3$,2Cl$^-$ (1 g, 1.3 mmol) and HO$_2$C—C$_8$F$_{16}$—CO$_2$H (625 mg, 1.3 mmol) were mixed together at 80° C. under vacuum for 2 h to lead to a waxy material.

Example 17

(CH$_3$CH$_2$CH$_2$CH$_2$CH$_2$CH$_2$)$_3$P$^+$—(CH$_2$)$_3$—NHCO—(CH$_2$)$_{10}$—CONH—(CH$_2$)$_3$—P$^+$—(CH$_2$CH$_2$CH$_2$CH$_2$CH$_3$)$_3$,2Cl$^-$ with EDTA. (CH$_3$CH$_2$CH$_2$CH$_2$CH$_2$CH$_2$)$_3$P$^+$—(CH$_2$)$_3$—NHCO—(CH$_2$)$_{10}$—CONH—(CH$_2$)$_3$—P$^+$(CH$_2$CH$_2$CH$_2$CH$_2$CH$_3$)$_3$,2Cl$^-$ (1 g, 1 mmol) and EDTA (153 mg, 0.5 mmol) were mixed together at 80° C. under vacuum for 2 h to lead to a solid material.

Example 18

(CH$_3$CH$_2$CH$_2$CH$_2$CH$_2$CH$_2$)$_3$P$^+$—(CH$_2$)$_9$CH$_3$,Cl$^-$ with EDTA. (CH$_3$CH$_2$CH$_2$CH$_2$CH$_2$CH$_2$)$_3$P$^+$—(CH$_2$)$_9$CH$_3$,Cl$^-$ (g, 2.15 mmol) and EDTA (315 mg, 1.08 mmol) were mixed together at 80° C. under vacuum for 2 h to lead to a liquid. The low viscous liquid is significantly different that the ionic liquids prepared with the di-phosphonium as described above.

Example 19

$(CH_3CH_2CH_2CH_2CH_2CH_2)_3P^+$—$C_{10}H_{20}$—$P^+(CH_2CH_2CH_2CH_2CH_2CH_3)_3, 2Cl^-$ with tetraethyl ester of EDTA. $(CH_3CH_2CH_2CH_2CH_2CH_2)_3P^+$—$C_{10}H_{20}$—$P^+(CH_2CH_2CH_2CH_2CH_2CH_3)_3, 2Cl^-$ (1 g, 1.3 mmol) and tetraethyl ester of EDTA (257 mg, 0.65 mmol) were mixed together at 80° C. under vacuum for 2 h to lead to a liquid. Again a low viscous liquid is formed due to the inability to form a network with the ester analog of EDTA and is significantly different that with EDTA.

Example 20

The material formed from mixing $(CH_3CH_2CH_2CH_2CH_2CH_2)_3P^+$—$C_{10}H_{20}$—$P^+(CH_2CH_2CH_2CH_2CH_2CH_3)_3, 2Cl^-$ with polyacrylic acid (240,000 Mw at 25% in water) can be pulled to form a fiber-like material.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A salt comprising an anionic component and a cationic component, wherein:
   said anionic component is selected from the group consisting of
   $[O_2CCH_2OCH_2CH_2OCH_2CH_2OCH_2CO_2]^{-2}$,
   $[O_2C$—$C_8F_{16}$—$CO_2]^{-2}$,
   $[O_2CCH_2OCH_2CH_2OCH_2CO_2]^{-2}$,
   $[O_2CC_{10}H_{20}CO_2]^{-2}$,
   [dicarboxy terminated poly(acrylonitrile-co-butadiene)]$^{-2}$, and
   $[(O_2CCH_2)_2NCH_2CH_2N(CH_2CO_2)_2]^{-4}$; and
   said cationic component is selected from the group consisting of
   [$^{Me}$Imid-$CH_2CH_2OCH_2CH_2OCH_2CH_2OCH_2CH_2$-Imid$^{Me}$]$^{+2}$,
   [$^{Me}$Imid-$CH_2CH_2OCH_2CH_2OCH_2CH_2$-Imid$^{Me}$]$^{+2}$, and
   [TIME$^{Me}$]$^{+3}$.

2. The salt of claim 1, wherein said anionic component is $[(O_2CCH_2)_2NCH_2CH_2N(CH_2CO_2)_2]^{-4}$; and said cationic component is [$^{Me}$Imid-$CH_2CH_2OCH_2CH_2OCH_2CH_2$-Imid$^{Me}$]$^{+2}$.

3. A salt comprising an anionic component and a cationic component, wherein:
   said anionic component is selected from the group consisting of
   $[O_2CCH_2OCH_2CH_2OCH_2CH_2OCH_2CO_2]^{-2}$,
   $[O_2C$—$C_8F_{16}$—$CO_2]^{-2}$,
   polyacrylic acid,
   $[O_2CCH_2OCH_2CH_2OCH_2CO_2]^{-2}$,
   $[O_2CC_{10}H_{20}CO_2]^{-2}$,
   [dicarboxy terminated poly(acrylonitrile-co-butadiene)]$^{-2}$, and
   $[(O_2CCH_2)_2NCH_2CH_2N(CH_2CO_2)_2]^{-4}$; and
   said cationic component is selected from the group consisting of
   [$^{Me}$Imid-$CH_2CH_2OCH_2CH_2OCH_2CH_2OCH_2CH_2$-Imid$^{Me}$]$^{+2}$,
   [$^{Me}$Imid-$CH_2CH_2OCH_2CH_2OCH_2CH_2$-Imid$^{Me}$]$^{+2}$,
   [TIME$^{Me}$]$^{+3}$,
   $[(H_3NCH_2CH_2)_3N]^{+3}$,
   $[H_3N$—$CH_2CH_2NHCH_2CH_2NHCH_2CH_2NH_3]^{+2}$,
   $[H_3NCH_2CH_2OCH_2CH_2OCH_2CH_2NH_3]^{+2}$,
   $[H_3NCH_2CH_2OCH_2CH_2OCH_2CH_2OCH_2CH_2NH_3]^{+2}$,
   $[(H_3NCH_2CH_2)_3N]^{+3}$,
   $[(NH_3CH_2CH_2)_3NH]^{+4}$,
   $[HC(O[CH_2CH(CH_3)O]_yCH_2CH(CH_3)NH_3)$—$(CH_2O[CH_2CH(CH_3)O]_xCH_2CH(CH_3)NH_3)$—$(CH_2O[CH_2CH(CH_3)O]_zCH_2CH(CH_3)NH_3)]^{+3}$,
   $[(CH_3CH_2CH_2CH_2CH_3CH_2)_3P$—$C_{10}H_{20}$—$P(CH_2CH_2CH_2CH_2CH_2CH_3)_3]^{+2}$, and
   $[(CH_3CH_2CH_2CH_2CH_2CH_2)_3P$—$(CH_2)_3$—$NHCO$—$(CH_2)_{10}$—$CONH$—$(CH_2)_3$—$P(CH_2CH_2CH_2CH_2CH_2CH_3)_3]^{+2}$;
   wherein x is 0-81 inclusive; y is 0-81 inclusive; z is 0-81 inclusive; and the sum of x, y and z is equal to 81.

* * * * *

UNITED STATES PATENT AND TRADEMARK OFFICE
CERTIFICATE OF CORRECTION

PATENT NO. : 8,367,845 B2
APPLICATION NO. : 12/297756
DATED : February 5, 2013
INVENTOR(S) : Mark W. Grinstaff et al.

Page 1 of 1

It is certified that error appears in the above-identified patent and that said Letters Patent is hereby corrected as shown below:

In the Claims:

Column 46, line 39, Claim 3 should read:
$[(CH_3CH_2CH_2CH_2CH_2CH_2)_3P-C_{10}H_{20}-P$ Signed and Sealed this
Twenty-seventh Day of August, 2013

Teresa Stanek Rea
*Acting Director of the United States Patent and Trademark Office*